US006559441B2

(12) United States Patent
Clemmer

(10) Patent No.: US 6,559,441 B2
(45) Date of Patent: *May 6, 2003

(54) ION SEPARATION INSTRUMENT

(75) Inventor: David E. Clemmer, Gosport, IN (US)

(73) Assignee: Advanced Research & Technology Institute, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/074,210

(22) Filed: Feb. 12, 2002

(65) Prior Publication Data

US 2002/0070339 A1 Jun. 13, 2002

Related U.S. Application Data

(63) Continuation of application No. 09/615,102, filed on Jul. 13, 2000, now Pat. No. 6,498,342, which is a continuation-in-part of application No. 09/313,492, filed on May 17, 1999, now Pat. No. 6,323,482, which is a continuation-in-part of application No. 08/867,245, filed on Jun. 2, 1997, now Pat. No. 5,905,258.

(51) Int. Cl.[7] .............................................. H01J 49/40
(52) U.S. Cl. ...................... 250/287; 73/19.02; 73/61.52
(58) Field of Search ........................ 250/287; 73/19.02, 73/61.52

(56) References Cited

U.S. PATENT DOCUMENTS

| 3,621,240 A | | 11/1971 | Cohen et al. ............. 250/41.96 |
|---|---|---|---|
| 3,626,179 A | * | 12/1971 | Cohen ......................... 250/287 |
| 3,668,383 A | * | 6/1972 | Carroll ........................ 250/287 |
| 3,812,355 A | | 5/1974 | Wernlund et al. ........... 250/283 |
| 3,845,301 A | | 10/1974 | Wernlund et al. ........... 250/287 |
| 3,902,064 A | | 8/1975 | Young ........................ 250/287 |
| 4,261,698 A | | 4/1981 | Carr et al. ................... 250/287 |
| 4,855,595 A | * | 8/1989 | Blanchard ................... 250/287 |
| 4,987,767 A | * | 1/1991 | Corrigan et al. ............. 250/287 |
| 5,070,240 A | | 12/1991 | Lee et al. .................... 250/288 |
| 5,117,107 A | | 5/1992 | Guilhaus et al. ............ 250/287 |
| 5,210,412 A | | 5/1993 | Levis et al. ................. 250/288 |
| 5,420,424 A | * | 5/1995 | Carnahan et al. ........... 250/287 |
| 5,504,326 A | | 4/1996 | Reilly et al. ................ 250/282 |
| 5,510,613 A | | 4/1996 | Reilly et al. ................ 250/287 |
| 5,622,824 A | | 4/1997 | Koster ........................ 250/282 |
| 5,640,011 A | | 6/1997 | Wells ......................... 250/282 |
| 5,763,878 A | | 6/1998 | Franzen ..................... 250/292 |
| 5,905,258 A | * | 5/1999 | Clemmer et al. ........... 250/287 |
| 6,323,482 B1 | * | 11/2001 | Clemmer et al. ........... 250/287 |

OTHER PUBLICATIONS

"Ion Mobility Spectrometry", Analytical Chemistry, vol. 62, No. 23, Dec. 1, 1990, pp. 1201A–1209A.
Abstract "Proceedings of the 44th ASMS Conference", (1996), R. Guevremont, K.W.M. Siu, and L. Ding, pate 1090.

(List continued on next page.)

*Primary Examiner*—Jack Berman
(74) *Attorney, Agent, or Firm*—Barnes & Thornburg

(57) ABSTRACT

An ion separation instrument includes an ion source coupled to at least a first ion mobility spectrometer having an ion outlet coupled to a mass spectrometer. In one embodiment, the ion source includes a molecule separation instrument operable to separate ions in time according to a molecular characteristic such as ion retention time. The resultant instrument is thus operable to provide molecular information separated in time as functions of retention time, ion mobility and ion mass/charge. In another embodiment, the ion separation instrument includes first and second ion mobility instruments disposed in a cascade arrangement between the ion source and mass spectrometer, wherein the two ion mobility instruments are operable to separate ions in time each according to different ion mobility functions. For example, the two ion mobility instruments may have different flight tube lengths, operate at different temperatures, operate in the presence of different electric fields and/or operate in the presence of different gases. The resultant instrument is thus operable to provide molecular information separated in time according to at least two different functions of ion mobility as well as ion mass/charge.

44 Claims, 19 Drawing Sheets-

OTHER PUBLICATIONS

PCT International Application No. PCT/US98/11129, International Publication No. WO 98/56029, published Dec. 10, 1998.

PCT International Application No. PCT/US97/14001, International Publication No. WO 98/07177, published Feb. 19, 1998.

Sheila C. Henderson et al., "ESI/Ion Trap/Ion Mobility/Time–of–Flight Mass Spectrometry for Rapid and Sensitive Analysis of Biomolecular Mixtures," Anal. Chem. 1999, 71, pp. 291–301.

Cherokee S. Hoaglud et al., "Three–Dimensional Ion Mobility/TOFMS Analysis of Electrosprayed Biomolecules," Anal. Chem. 1998, pp. 2236–2242.

Roger Guevremont et al., "Combined Ion Mobility/Time–of–Flight Mass Spectrometry Study of Electrospray–Generated Ions," Anal. Chem. 1997, 69, pp. 3959–3965.

PCT International Application No. PCT/US99/01292, International Publication No. WO 99/38194, published Jul. 29, 1999.

European Patent Publication No. EP 0898 297 A2, Bulletin 1999/08, published Feb. 24, 1999.

R. Graham Cooks et al., "Spectrometers, Mass," XP–002155452, Encyclopedia of Applied Physics, vol. 19, 1997 VCH Publishers, Inc., pp. 289–330.

Charles S. Harden et al., "Detection of Methyl Isocyanate in Air with the Use of Hand–Held Ion Mobility Spectrometers," Field Analytical Chemistry and Technology, 1997 John Wiley & Sons, Inc, pp. 285–294.

Anne E. Counterman et al., "High–Order Structure and Dissociation of Gaseous Peptide Aggregates that are Hidden in Mass Spectra," Am. Soc. For Mass Spec., 1998 Elsevier Science Inc., pp. 743–759.

Roger Guevremont et al., "High Field Asymmetric Waveform Ion Mobility Spectrometry—Mass Spectrometry: An Investigation of Leucine Enkephalin Ions Produced by Electrospray Ionization," Am Soc. For Mass Spec., 1999 Elsevier Science, Inc., pp. 492–501.

* cited by examiner

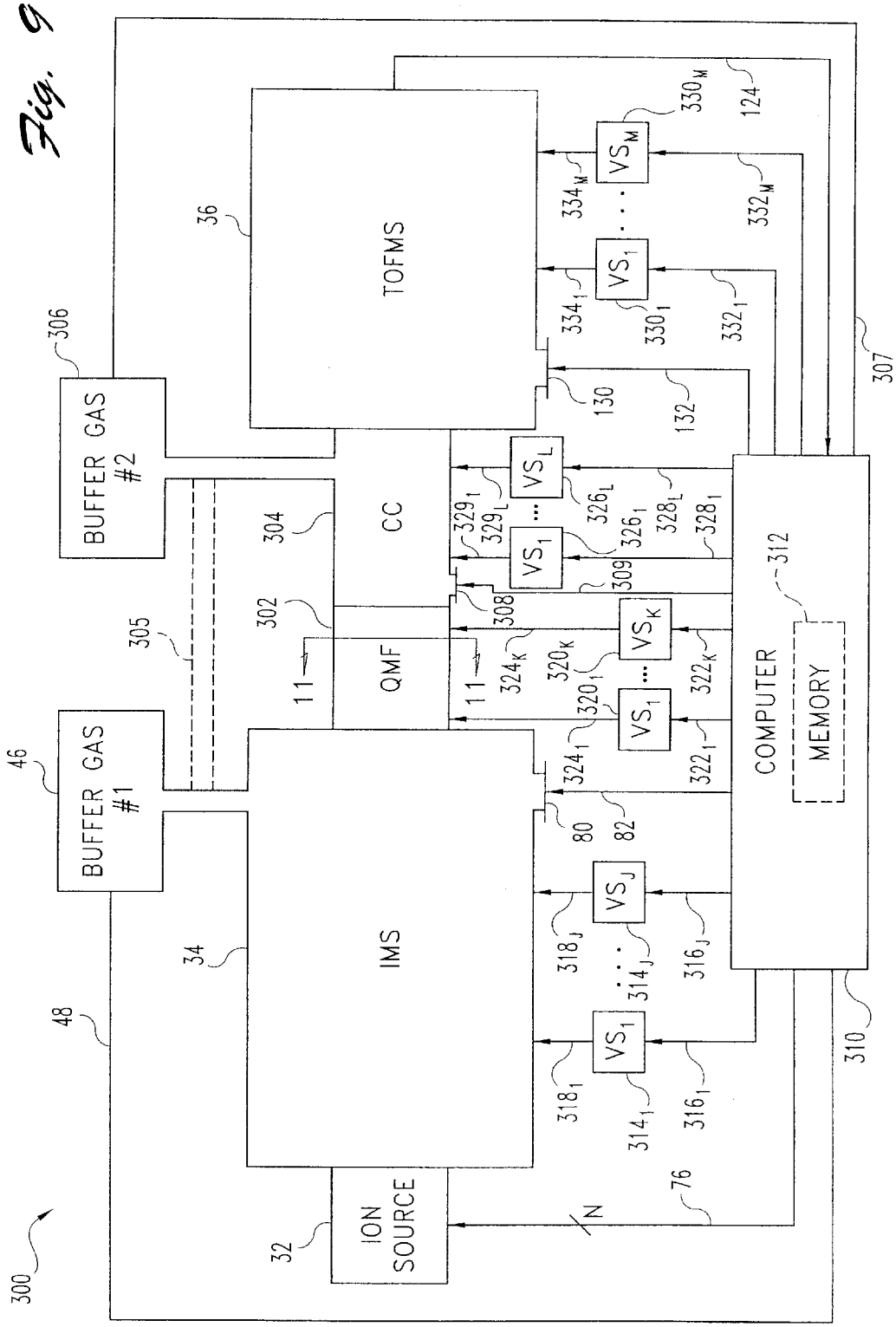

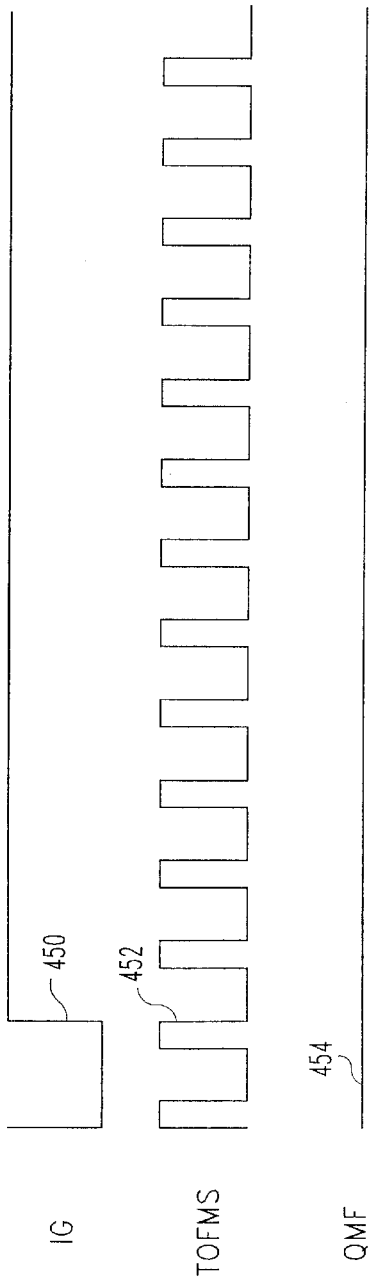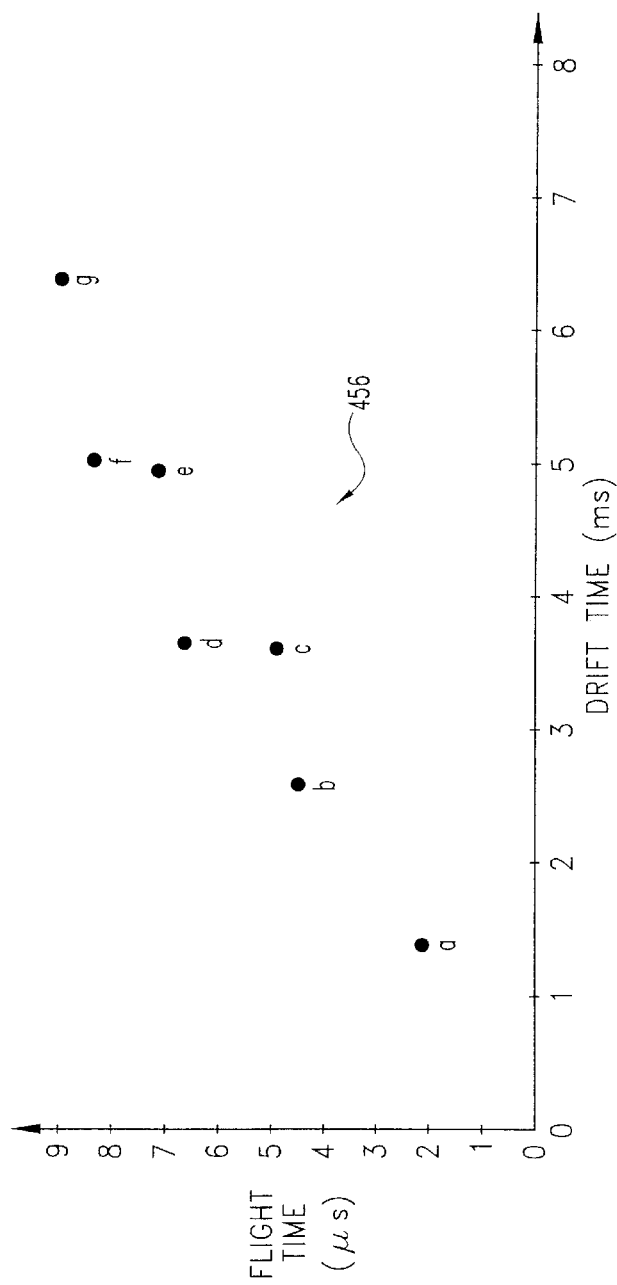
Fig. 14A
Fig. 14B
Fig. 14C
Fig. 14D

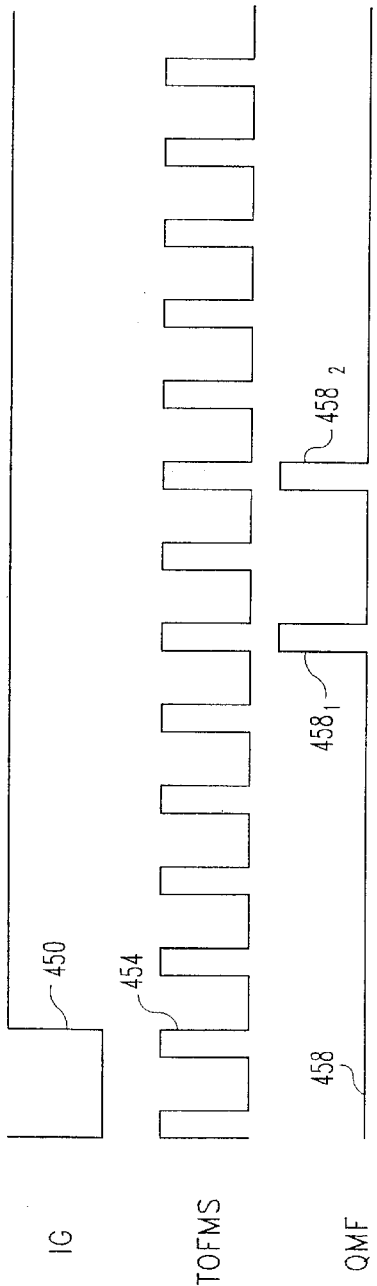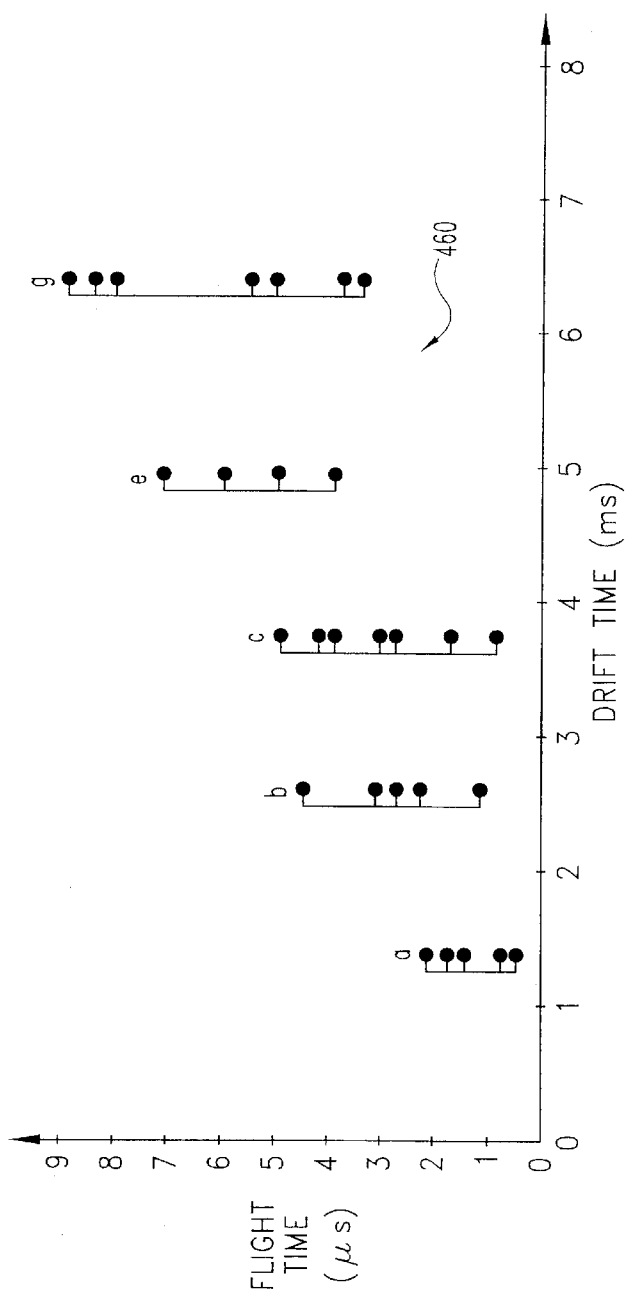
Fig. 15A
Fig. 15B
Fig. 15C
Fig. 15D

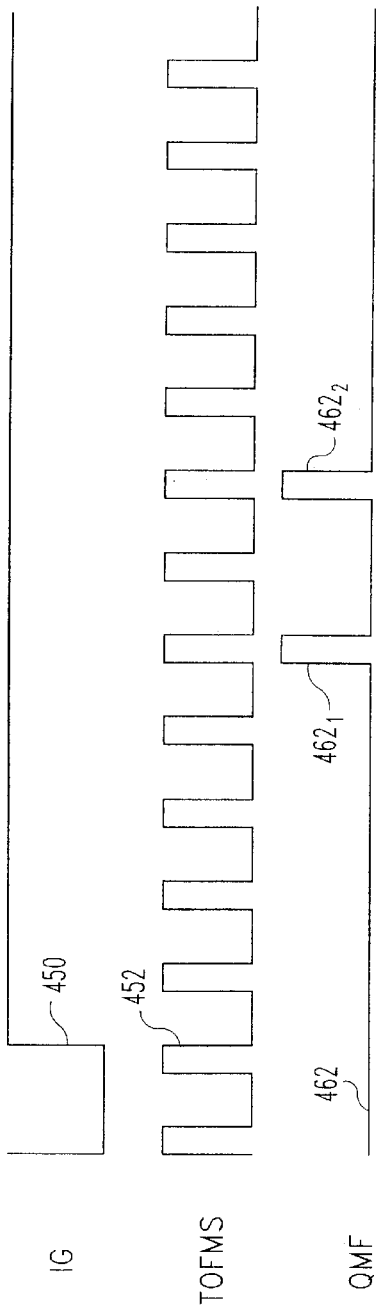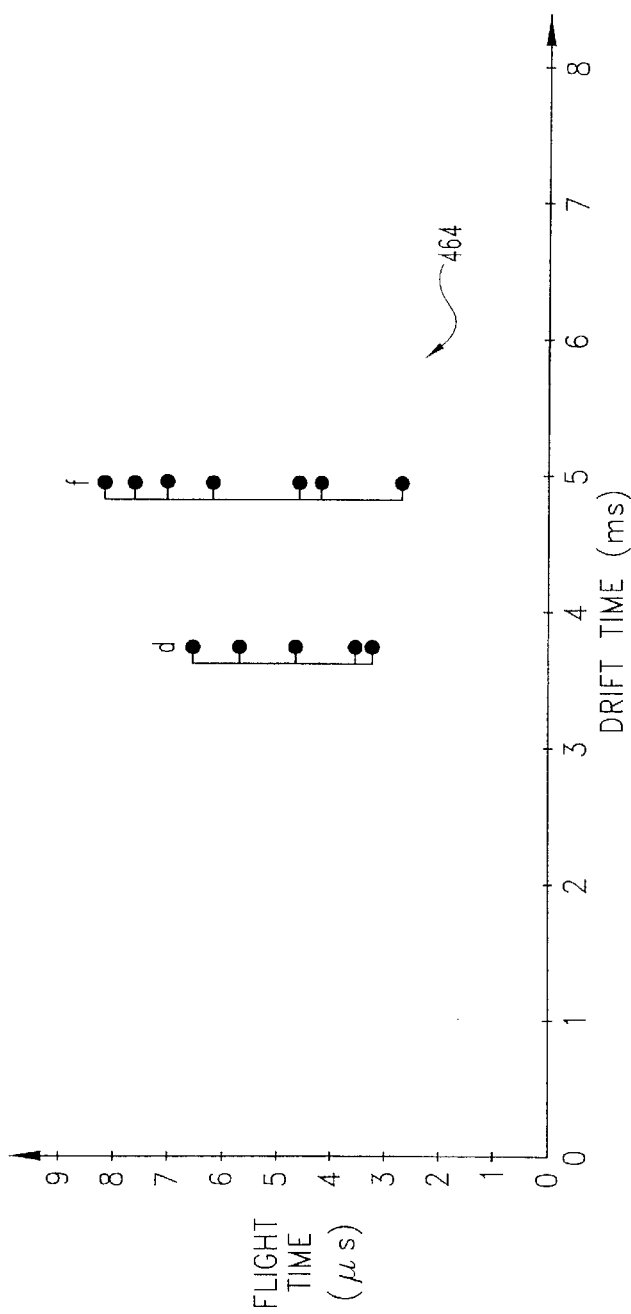
Fig. 16A
Fig. 16B
Fig. 16C
Fig. 16D

ION SEPARATION INSTRUMENT

CROSS-REFERENCE TO RELATED U.S. APPLICATION

This is a continuation of application Ser. No. 09/615,102, now U.S. Pat. No. 6,498,342, filed Jul. 13, 2000, which is a continuation-in-part of application No. 09/313,492 filed May 17, 1999 U.S. Pat. No. 6,323,482, which is a continuation-in-part of application No. 08/867,245 filed Jun. 2, 1997 U.S. Pat. No. 5,905,258.

FIELD OF THE INVENTION

The present invention relates generally to instrumentation for characterization of molecules based at least on their structures and mass-to-charge ratios as gas-phase ions, and more specifically to such instrumentation which provides for rapid and sensitive analysis of composition, sequence, and/or structural information relating to organic molecules, including biomolecules, and inorganic molecules.

BACKGROUND OF THE INVENTION

Biological molecules, such as DNA, RNA, proteins, carbohydrates and glycoconjugates, are comprised of repeating subunits typically referred to as residues. The sequence of such residues ultimately defines the structure and function of the biomolecule and determines how it will interact with other molecules.

A central part of almost all conventional sequencing strategies is the analysis of complex sets of sequence-related molecular fragments by chromatography or by polyacrylamide gel electrophoresis (PAGE). PAGE-based automated sequencing instruments currently exist and typically require a number of fluorescent dyes to be incorporated into the base-specifically terminated biomolecule product, which is then processed through the polyacrylamide gel. The discrete-length product molecules are detected near the bottom of the gel by their emitted fluorescence following excitation by a radiation source.

Such automated instruments are typically capable of generating sequence information for biomolecules having 500 or more residues at a rate of 10–20 times faster than manual methods. However, both the manual and automated PAGE techniques suffer from several drawbacks. For example, both approaches are labor-intensive since a gel must be prepared for each sequencing run. Also, while automated PAGE systems may offer faster analysis times than a manual approach, the accuracy of such systems is limited by artifacts generated by non-uniform gel matrices and other factors. Such automated systems are generally not equipped to accurately process the effects of such artifacts, which are typically manifested as "smiling" compressions, faint ghost bands, and the like. Manual interpretation of such results is therefore often required which significantly increases analysis time.

Researchers have, within the past several years, recognized a need for more rapid and sensitive techniques for analyzing the structure and sequences of biomolecules. Mass spectrometry (MS) techniques, such as time-of-flight mass spectrometry (TOFMS) and Fourier Transform ion-cyclotron-resonance mass spectroscopy, are well known techniques for quickly and accurately providing ion mass information from which sequence and structural determinations can be made. As is known in the art, TOFMS systems accelerate ions, via an electric field, toward a field-free flight tube which terminates at an ion detector. In accordance with known TOFMS principles, ion flight time is a function of ion mass so that ions having less mass arrive at the detector more quickly than those having greater mass. Ion mass can thus be computed from ion flight time through the instrument. FIG. 1 demonstrates this principle for a cytochrome-c sample, having a known mass to charge ratio (m/z) of 12,360 da, and a lysozyme sample, having a known mass to charge ratio (m/z) of 14,306 da. In FIG. 1, signal peak 10, having a flight time of approximately 40.52 $\mu s$ corresponds to the lighter cytochrome-c sample, and signal peak 12, having a flight time of approximately 41.04 $\mu s$, corresponds to the heavier lysozyme sample.

Due to the significantly decreased sample preparation and analysis times of MS techniques over the above-described PAGE technique, several MS sequencing strategies have recently been developed. Such MS sequencing techniques are generally operable to measure the change in mass of a biomolecule as residues are sequentially removed from its end. Examples of two such techniques, each involving elaborate pre-MS processing techniques, are described in U.S. Pat. Nos. 5,210,412 to Levis et al. and 5,622,824 to Köster.

In order to provide for the capability of determining sequence and structural information for large biomolecules, it has been recognized that MS techniques must accordingly be capable of generating large ions. Currently, at least two techniques are known for generating large ions for spectral analysis; namely electrospray ionization (ESI) and matrix assisted laser desorption ionization (MALDI). While both large ion generating techniques are readily available, known MS techniques are limited in both the quantity and quality of discernable information. Specifically, for large biomolecules, defined here as those containing at least 50 residues, mass spectra of parent and sequence related fragment ions become congested to the degree that mass (TOF) peaks overlap.

One solution to the problem of congested mass spectra is to increase the mass resolution capability of the MS instrument. Recent efforts at increasing such resolution have been successful, and complete sequence information for a 50 base pair DNA has been obtained using a Fourier Transform ion cyclotron resonance (FTICR) instrument. However, such instruments are extremely expensive, not readily available, and because of their extremely high vacuum requirements, they are generally not suitable for routinely sequencing large numbers of samples.

Another solution to the problem of congested mass spectra is to pre-separate the bulk of ions in time prior to supplying them to the ion acceleration region of the MS instrument. Mass spectrometry can then be performed sequentially on "packets" of separated ion samples, rather than simultaneously on the bulk of the generated ions. In this manner, mass spectral information provided by the MS instrument may be spread out over time in a dimension other than mass to thereby reduce the localized congestion of mass information associated with the bulk ion analysis.

One known ion separation technique which may be used to pre-separate the bulk of the ions in time prior to MS analysis is ion mobility spectrometry (IMS). As is known in the art, IMS instruments typically include a pressurized static buffer gas contained in a drift tube which defines a constant electric field from one end of the tube to the other. Gaseous ions entering the constant electric field area are accelerated thereby and experience repeated collisions with the buffer gas molecules as they travel through the drift tube. As a result of the repeated accelerations and collisions, each of the gaseous ions achieves a constant velocity through the drift tube. The ratio of ion velocity to the magnitude of the electric field defines an ion mobility, wherein the mobility of any given ion through a high pressure buffer gas is a function of the collision cross-section of the ion with the buffer gas and the charge of the ion. Generally, compact conformers, i.e. those having smaller collision cross-sectional areas, have higher mobilities, and hence higher velocities through the buffer gas, than diffuse conformers of the same mass, i.e. those having larger collision cross-sectional areas. Thus, ions having larger collision cross-sections move more slowly through the drift tube of an IMS instrument than those having smaller collision cross-sections, even though the ions having smaller collision cross-sections may have greater mass than those having higher collision cross-sections. This concept is illustrated in FIG. 2 which shows drift times through a conventional IMS instrument for three ions, each having a different mass and shape (collision cross-section). As is evident from FIG. 2, the most compact ion 14 (which appears to have the greatest mass) has the shortest drift time peak 16 of approximately 5.0 ms, the most diffuse ion 18 has the longest drift time peak 20 of approximately 7.4 ms, and the ion 22 having a collision cross-section between that of ion 14 and ion 18 (which also appears to have the least mass), has a drift time peak 24 of approximately 6.1 ms.

Referring now to FIG. 3, an ion time-of-flight spectrum 26, obtained from a known time-of-flight mass spectrometer, is shown plotted vs. ion drift time. In-this figure, ions of different-mass are dispersed over different times of flight in the mass spectrometer. However, due to the limited resolution of the mass spectrometer, ions are not completely separated in the spectrum, i.e. dots corresponding to different ions overlap. When compared with FIG. 6, which will be discussed more fully in the DESCRIPTION OF THE PREFERRED EMBODIMENTS section, it is evident that different ions can be better resolved by an instrument that separates ions in two dimensions, namely ion mobility and ion mass.

Guevremont et al. have recently modified an existing IMS/MS instrument to convert a quadrupole MS to a TOFMS [R. Guevremont, K. W. M. Siu, and L. Ding, PROCEEDINGS OF THE 44$^{TH}$ ASMS CONFERENCE, (1996), Abstract]. Ions are generated in the Guevremont et al. instrument via electrospray, and 5 ms packets are gated into the IMS instrument. The ion packets produced by the IMS instrument are passed through a small opening into an ion acceleration region of the TOFMS.

While Guevremont et al. have had some experimental success in coupling an IMS instrument to a TOFMS instrument, their resulting instrumentation and techniques have several drawbacks associated therewith. For example, since the Guevremont et al. abstract discusses using 5 ms gate pulses to admit ions into the IMS instrument, it is noted that the resultant IMS spectrum has low resolution with at least 5 ms peak widths. Secondly, because the drift tube and ion flight tube of the Guevremont et al. instrument are colinear, any spatial and temporal spread in an ion packet leaving the IMS leads directly to a spatial and temporal spread of ions in the ion acceleration region of the TOFMS. These two characteristics lead to poor mass resolution in the TOFMS. The combination of low resolution in the IMS and low resolution in the TOFMS makes this instrument incapable of resolving complex mixtures. What is therefore needed is a hybrid IMS/TOFMS instrument optimized to resolve complex mixtures. Such an instrument should ideally provide for optimization of the ion mobility spectrum as well as optimization of the mass spectrum. Moreover, such a system should provide for an optimum interface between the two instruments to thereby maximize the capabilities of the TOFMS.

SUMMARY OF THE INVENTION

The foregoing drawbacks associated with the prior art systems discussed in the BACKGROUND section are addressed by the present invention. In accordance with one aspect of the present invention, a method of separating ions in time comprises the steps of separating a bulk of ions in time as a function of a first molecular characteristic, sequentially separating in time as a function of ion mobility at least some of the ions previously separated in time as a function of a first molecular characteristic, and sequentially separating in time as a function of ion mass at least some of the ions previously separated in time as a function of ion mobility.

In accordance with another aspect of the present invention, an apparatus for separating ions in time comprises means for separating a bulk of ions in time as a function of a first molecular characteristic, an ion mobility spectrometer (IMS) having an ion inlet coupled to the means for separating a bulk of ions in time as a function of a first molecular characteristic and an ion outlet, wherein the IMS is operable to separate ions in time as a function of ion mobility. A mass spectrometer (MS) is further included and has an ion acceleration region coupled to the ion outlet of the IMS, wherein the MS is operable to separate ions in time as a function of ion mass.

In accordance with a further aspect of the present invention, a method of separating ions in time comprises the steps of separating a bulk of ions in time according to a first function of ion mobility, sequentially separating in time according to a second function of ion mobility at least some of the ions separated in time according to the first function of ion mobility, wherein the second function of ion mobility is different from the first function of mobility, and sequentially separating in time as a function of ion mass at least some of the ions separated in time according to the second function of ion mobility.

In accordance with still another aspect of the present invention, an apparatus for separating ions in time comprises a first ion mobility spectrometer (IMS1) having an ion inlet and an ion outlet, wherein the IMS1 is operable to separate ions in time according to a first function of ion mobility and a second ion mobility spectrometer (IMS2) having an ion inlet coupled to the ion outlet of the IMS1 and an ion outlet, wherein the IMS2 is operable to separate ions in time according to a second function of ion mobility different from the first function of ion mobility. A mass spectrometer is also included and has an ion acceleration region coupled to the ion outlet of the IMS2, wherein the mass spectrometer is operable to separate ions in time as a function of ion mass.

One object of the present invention is to provide instrumentation for rapid analysis and sequencing of large biomolecules, as well as analysis of mixtures of organic and inorganic molecules.

Another object of the present invention is to provide an ion mobility and mass spectrometer for composition, sequence and structural analysis of biomolecules.

Yet another object of the present invention is to provide such an instrument operable to produce molecular information separated in time according to at least three different molecular characteristic functions.

Still another object of the present invention is to provide such an instrument wherein two of the three different molecular characteristic functions are ion mobility and ion mass/charge, and wherein the third molecular characteristic function may be ion retention time, a second different ion mobility or the like.

Still a further object of the present invention is to provide a technique for operating such an instrument in obtaining sequencing information.

These and other objects of the present invention will become more apparent from the following description of the preferred embodiments.

BRIEF DESCRIPTION OF THE DRAWINGS

FIG. 9 is a block diagram illustration of another alternate embodiment of an ion mobility and time-of-flight mass spectrometer, in accordance with the present invention.

FIG. 14 is composed of FIGS. 14A–14D and illustrates an example ion mass/mobility spectrum resulting from a first pass through the process illustrated in FIG. 13.

FIG. 15 is composed of FIGS. 15A–15D and illustrates an example ion mass/mobility spectrum resulting from a second pass through the process illustrated in FIG. 13.

FIG. 16 is composed of FIGS. 16A–16D and illustrates an example ion mass/mobility spectrum resulting from a third pass through the process illustrated in FIG. 13.

DESCRIPTION OF THE PREFERRED EMBODIMENTS

Figure 1:
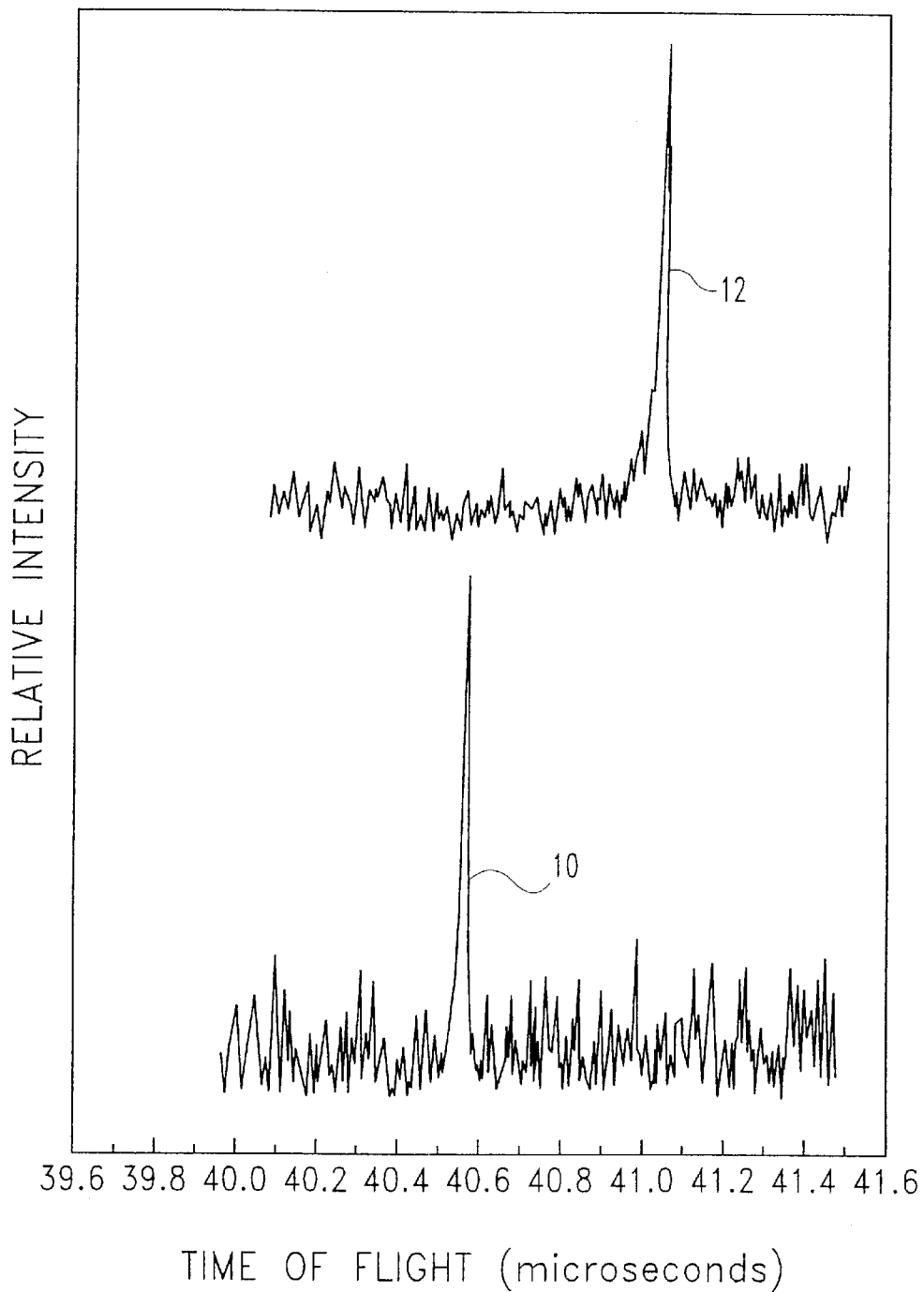
FIG. 1 is a MALDI-TOF mass spectrum of cytochrome-c and lysozyme.
Figure 2:
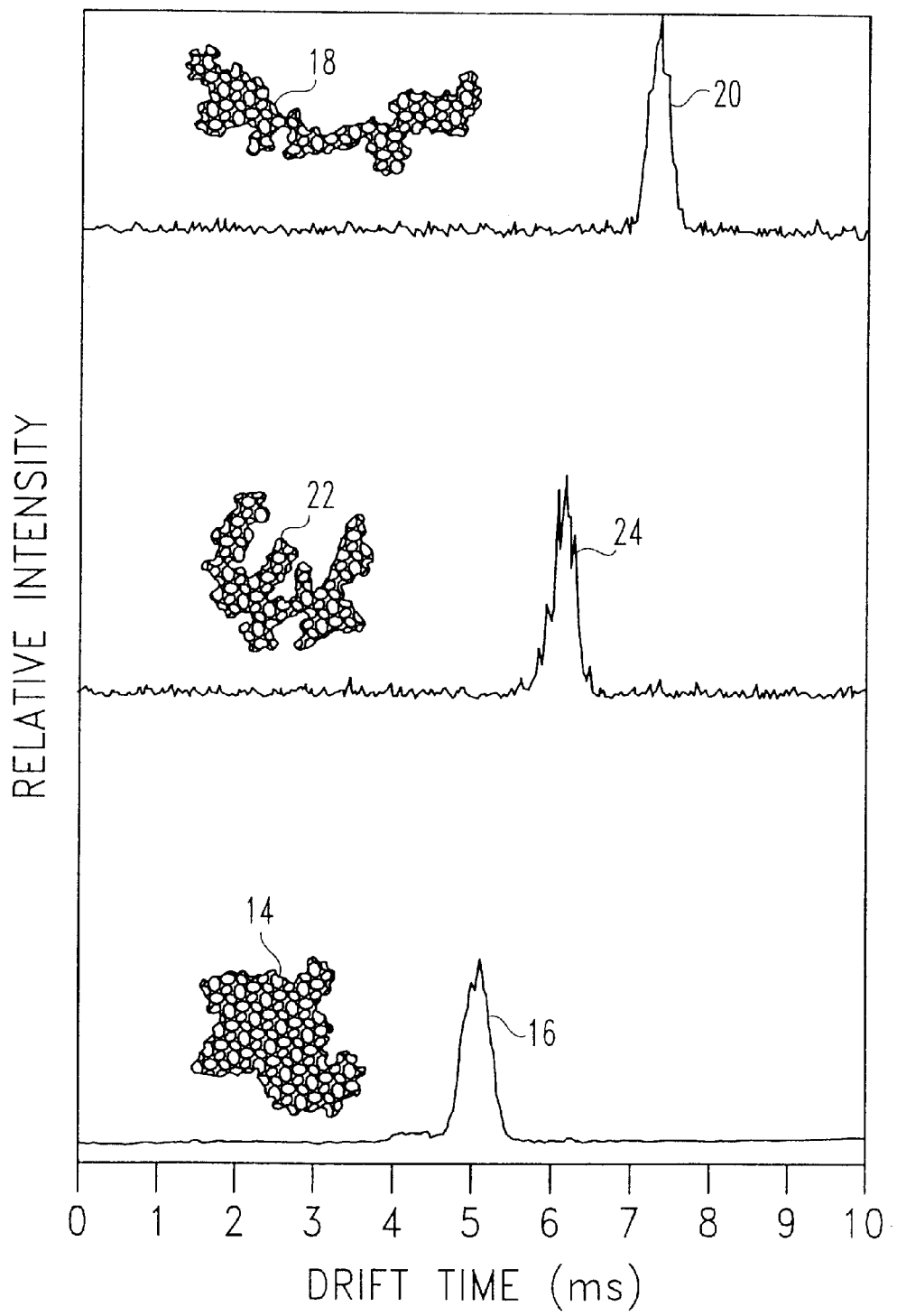
FIG. 2 is an IMS drift time distribution for three ions having different collision cross-sections.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 4:
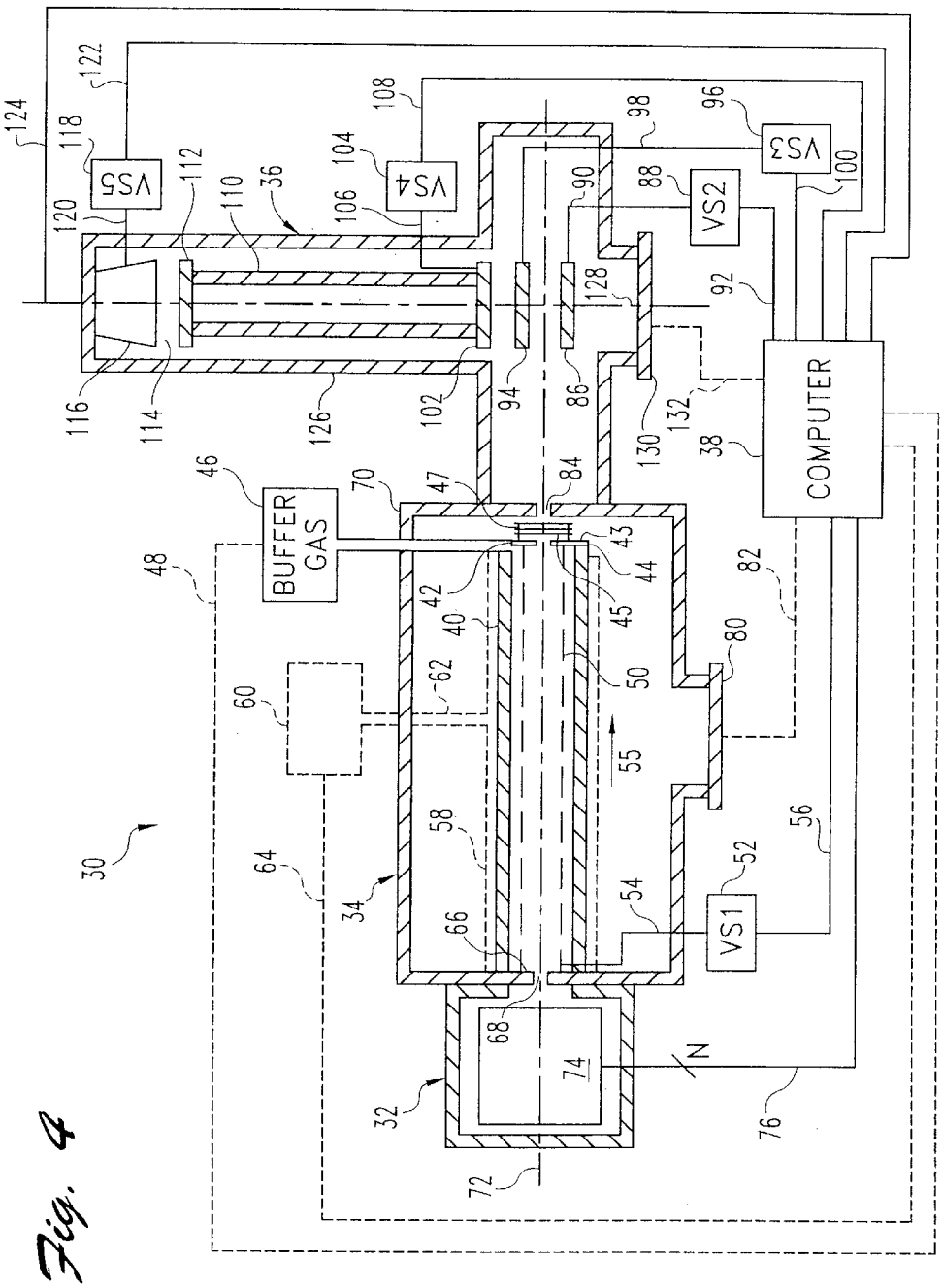
FIG. 4 is a cross-section and schematic diagram of one embodiment of a hybrid ion mobility and time-of-flight mass spectrometer, in accordance with the present invention.

Referring now to FIG. 4, one preferred embodiment of a hybrid ion mobility and time-of-flight mass spectrometer instrument 30, in accordance with the present invention, is shown. Instrument 30 includes, as its basic components, an ion source region 32 in communication with an ion mobility spectrometer 34, which itself is in communication with a mass spectrometer 36. A computer 38 is provided for controlling at least some portions of the instrument 30 as well as for collecting ion information from mass spectrometer 36. Computer 38 is preferably a personal computer (PC) of known construction having at least a known 386 processor, although the present invention contemplates that computer 38 may be any known computer, controller or data processor capable of controlling instrument 30, as set forth in greater detail hereinafter, and of collecting and processing ion information from mass spectrometer 36.

Preferably, mass spectrometer 36 is of the linear time-of-flight type, although the present invention contemplates that spectrometer 36 may alternatively be a known reflectron time-of-flight mass spectrometer, multi-pass time-of-flight mass spectrometer, Fourier Transform ion-cyclotron-resonance (FTICR-MS) mass spectrometer or other known mass spectrometer. Throughout this description, any mass spectrometer will typically be referred to as a time-of-flight mass spectrometer (TOFMS), although it is to be understood that any of the foregoing mass spectrometer instruments may be substituted therefore without detracting from the scope of the present invention. In any case, TOFMS 36 is, in one preferred embodiment, configured to maximize mass resolution by minimizing the deleterious effects of initial ion position and initial ion velocity distributions. Details of such a TOFMS configuration and operation thereof are given in U.S. Pat. Nos. 5,504,326, 5,510,613 and 5,712,479 to Reilly et al., all assigned to the assignee of the present invention, and the contents of which are all incorporated herein by reference.

Ion mobility spectrometer (IMS) 34 includes a drift tube 40 having a gas port 42 disposed adjacent to an ion exit end 44 of tube 40, wherein port 42 is connected to a source of buffer gas 46. The flow rate of buffer gas may be controlled by computer 38 via signal path 48, or may alternatively be controlled by a manually actuated valve (not shown). Ion exit end 44 of drift tube 40 includes an endplate 43 attached thereto, wherein endplate 43 defines an opening, or ion aperture, 45 therethrough.

Drift tube 40 includes a number of guard rings 50 distributed along its inner surface, wherein the guard rings 50 are interconnected by equivalent-valued resistors (not shown). The guard ring positioned most adjacent to ion source region 32 is connected to a voltage source VS1 52 via signal path 54, and source 52 is preferably controlled by computer 38 via signal path 56, although the present invention contemplates controlling source 52 via a manual actuator (not shown). The drift tube 40 defines a longitudinal axis 72 therethrough which will be referred to hereinafter as the drift tube axis 72. Voltage source 52 is preferably set to a positive voltage to thereby establish a constant electric field directed along axis 72 in a direction indicated by arrow 55. Those skilled in the art will recognize that the importance of the guard ring and voltage source arrangement of the spectrometer 34 lies not in its specific structure, but in its ability to establish, as accurately as possible, a constant electric field in the direction of arrow 55. In this sense, the present invention contemplates that any known structure or arrangement may be used to establish such an electric field within drift tube 40 in the direction of arrow 55. It is to be understood, however, that a constant electric field in the direction of arrow 55 is established to accelerate positively charged ions toward tube end 44, and that such an electric field may be reversed to thereby accelerate negatively charged ions toward tube end 44.

Drift tube 40 may optionally be surrounded by a variable temperature housing 58 which is connected to a variable temperature source 60 via path 62, all of which are shown in phantom. In one embodiment, variable temperature source 60 is a fluid holding tank and path 62 is a conduit leading to housing 58 which, in this case, is preferably sealed. A return conduit (not shown) is also connected to the fluid holding tank so that fluid from within the tank may be circulated through housing 58. The fluid within the fluid holding tank may be a heated or cooled gas or liquid such as, for example, liquid nitrogen. In an alternate embodiment, variable temperature source 60 is a known electrically actuatable temperature controller, and path 62 comprises a pair of electrical conductors connected between the controller and housing 58. In operation, temperature controller 60 is operable to heat or cool housing 58 as desired. Regardless of the particular embodiment of housing 58, source 60 and path 62, the present invention contemplates that source 60 may furthermore be controlled by computer 38 via signal path 64.

Drift tube 40 is further surrounded by a housing 70 which defines a tube end 66 covering an ion entrance end thereof, wherein tube end 66 defines an opening, or ion aperture, 68 therethrough, and an ion exit opening, or aperture, 84 adjacent to endplate 43. Preferably, ion optics 47 are positioned between openings 45 and 84 to focus ions exiting opening 45 into an ion acceleration region of TOFMS 36. Openings 45, 68 and 84 are preferably bisected by drift tube axis 72. An ion source 74, which will be described more fully hereinafter, is positioned within ion source region 32 and is operable, preferably under the control of computer 38 via a number, N, of signal paths 76, wherein N may be any positive integer, to direct ions within the spectrometer 34 via opening 68. Ions entering drift tube 40 separate in time as a function of their individual mobilities, as discussed hereinabove, and are sequentially directed through opening 70 toward TOFMS 36.

Housing 70 includes a pump 80 for controlling the pressure of the buffer gas. Preferably, pump 80 is a diffusion pump, the operation of which may be controlled by computer 38 via signal path 82. Alternatively, pump 80 may be manually controlled by a manual pump actuator (not shown). In any case, pump 80 is operable to establish a desired pressure of the static buffer gas within drift tube 40. In accordance with known IMS techniques, the buffer gas within drift tube 40 may typically be set within the range of between approximately one and a few thousand Torr.

TOFMS 36 is preferably surrounded by a housing 126 that is attached to IMS 34. TOFMS 36 includes a first electrically conductive grid or plate 86 connected to a second voltage source VS2 88 via signal path 90, which is preferably controlled by computer 38 via signal path 92. A second electrically conductive grid or plate 94 is connected to a third voltage source VS3 96 via signal path 98, which is preferably controlled by computer 38 via signal path 100. A third electrically conductive grid or plate 102 is connected to a fourth voltage source VS4 via signal path 106, which is preferably controlled by computer 38 via signal path 108. Grids or plates 86, 94 and 102 define first and second ion acceleration regions therebetween as is known in the art, and which will be more fully described hereinafter. Those skilled in the art will recognize that other known ion acceleration region structures may be used with TOFMS 36, such as, for example, positioning a fourth grid or plate between grids or plates 94 and 102.

Grid or plate 102 has a plate surface attached to one end of a flight tube 110, the opposite end of which is attached to a surface of a fourth electrically conductive grid or plate 112. An ion detector 116 is disposed adjacent to grid or plate 112 with an air gap 114 defined therebetween. Ion detector 116 is connected to a fifth voltage source VS5 118 via signal path 120, which is preferably controlled by computer 38 via signal path 122. Ion detector 116 further has a signal output connected to computer 38 via signal path 124, whereby detector 116 is operable to provide ion arrival time information to computer 38. Grids or plates 86, 94, 102 and 112 are preferably arranged in juxtaposition with each other such that all plate surfaces having greatest surface area are parallel with each other as well as to the surface of the ion detector 116, and are further preferably perpendicular to a longitudinal axis 128 defined centrally through the flight tube 110, which will hereinafter be referred to as the flight tube axis 128.

TOFMS 36 further includes a pump 130 for controlling the vacuum of the TOFMS chamber defined by housing 126. Preferably, pump 130 is a diffusion pump, the operation of which may be controlled by computer 38 via signal path 132. Alternatively, pump 130 may be manually controlled by a manual pump actuator (not shown). In any case, pump 130 is operable to establish a desired vacuum within housing 126 which may be set, in accordance with know TOFMS operating techniques, to within the range of between approximately $10^{-4}$ and $10^{-10}$ Torr.

In the instrument 30 illustrated in FIG. 4, TOFMS 36 is preferably arranged relative to IMS 34 such that the flight tube axis 128 is perpendicular to the drift tube axis 72. Moreover, TOFMS 36 is preferably positioned relative to IMS 34 such that the drift tube axis 72 and the flight tube axis 128 bisect within the first ion acceleration region defined between grids or plates j86 and 94. In an alternative configuration of TOFMS 36, grid or plate 94 may be omitted, and the TOFMS 36 need then be positioned relative to IMS 34 such that the drift tube axis 72 bisects the flight tube axis 128 within the ion acceleration region defined between grids or plates 86 and 102. In either case, TOFMS is preferably positioned relative to IMS 34 such that the drift tube axis 72 bisects the flight tube axis 128 approximately centrally within the region of interest.

In the operation of instrument 30, ions are generated by ion source 74, in accordance with one or more ion generation techniques described hereinafter, and are supplied to IMS 34 via IMS inlet opening 68. A buffer gas typically used in IMS instruments 34 is supplied to drift tube 40 via buffer gas source 46, wherein the buffer gas is regulated to a desired pressure via pump 80, buffer gas source 46 or a combination thereof. Typically, the buffer gas is regulated to a pressure of between approximately 1 and a few thousand Torr. Voltage source 52 supplies a voltage sufficient to generate a constant electric field along the drift tube axis in a direction indicated by arrow 55.

In accordance with known IMS 34 operation, ions entering IMS inlet opening 68 travel through drift tube 40 toward IMS outlet opening 84, wherein the ions separate in time according to their individual mobilities. Ions having low mobility lag behind those having higher mobility, wherein ion mobilities are largely a function of their collision cross-sections. As a result, the more compact ions arrive at the IMS outlet opening 84 more quickly than more diffuse ions. Those skilled in the art will recognize that the temperature of drift tube 40 may also be controlled via variable temperature source 60 so that ion mobility analysis may be performed as a function of temperature.

TOFMS 36 is operable to accelerate ions from the space defined between grids or plates 86 and 94 toward a field-free flight tube 110, wherein the ions separate in time according to their individual masses. Generally, ions having less mass will reach the detector 116 more quickly than those having greater mass. The detector 116 is operable to detect arrival times of the ions thereat and provide signals corresponding thereto to computer 38 via signal path 124.

As set forth in greater detail in U.S. Pat. Nos. 5,504,326, 5,510,613 and 5,712,479 to Reilly et al., which have been incorporated herein by reference, voltage sources VS2 88, VS3 96 and VS4 104 are typically controlled by computer 38 to initially establish voltages at grids or plates 86, 94 and 102 that match the voltage level associated with IMS 34 (which is set by voltage source VS1 52). Depending upon various instrument parameters, such as the length of flight tube 110, the distances between grids or plates 88, 94, 102 and 112, and the distance 114 between grid or plate, 112 and detector 116, as well as estimates of initial ion position or initial ion velocity within the space defined between grids or plates 86 and 94, computer 38 is operable to control sources 88, 96 and/or 104 to instantaneously increase the electric field between grids or plates 86, 94 and 102 to thereby create an ion drawout electric field therebetween which accelerates ions between these grids toward flight tube 110. Preferably, the pulsed ion drawout electric field is in a direction from grid or plate 86 toward flight tube 110 to thereby accelerate positively charged ions toward the flight tube 110. Those skilled in the art will recognize, however, that this electric field may alternatively be reversed to accelerate negatively charged ions toward the flight tube 110.

In any event, ions within the space defined between grids or plates 86 and 94 are accelerated by the pulsed ion drawout electric field to the space defined between grids or plates 94 and 102. Due to the fact that ions entering the region defined between grids or plates 86 and 94 along axis 72 have a narrow spatial distribution, due to focusing of the ions into this region via ion optics 47, and a small velocity component along axis 128, it is possible to choose the pulsed voltage applied to grids or plates 86 and/or 94 in such a way as to obtain sharp TOFMS peaks. The goal of the pulsed ion drawout electric field and the subsequent acceleration of the ions between grids or plates 94 and 102 is to provide all ions reaching grid or plate 102 with substantially the same kinetic energy. The flight tube 110 has no electric field associated therewith so that the ions drift from grid or plate 102 toward detector 116, wherein the ions separate in time as a function of their individual masses as described hereinabove. Computer 38 typically controls voltage source VS5 118 to supply a voltage thereto during detection times to thereby increase the gain of detector 116 as is known in the art. Pump 130 controls the vacuum within TOFMS 36, and pump 130 is preferably controlled by computer 38 via signal path 132. TOFMS 36 is typically operated between $10^{-4}$ and $10^{-10}$ Torr.

In the embodiment 30 of the hybrid IMS/TOFMS instrument illustrated in FIG. 4, drift tube axis 72 preferably bisects the space defined between grids or plates 86 and 94 of TOFMS 36, and is perpendicular to flight tube axis 128. The present invention alternatively contemplates arranging TOFMS 36 relative to IMS 34 such that the drift tube axis 72 passes between grids or plates 86 and 94 perpendicular to flight tube axis 128, but at some other known distance relative to either of the grids or plates 86 and 94. In either case, the foregoing structural positioning of TOFMS 36 relative to IMS 34 provides advantages over non-perpendicular arrangements of the drift tube axis 72 relative to the flight tube axis 128. For example, such a perpendicular arrangement ensures that ion packets entering the ion acceleration region defined between grids or plates 86 and 94 from IMS 34 will have constant and relatively well defined initial ion positions as they travel therebetween along axis 72. As discussed briefly hereinabove, ion optics 47 focus ions into the ion acceleration region to thereby minimize spatial distribution of the ions. Moreover, since axis 72 is parallel with grids or plates 86 and o4, ion position with respect to axis 128 will remain relatively constant. This feature provides for the ability to accurately estimate initial ion position within the ion acceleration region defined between grids or plates 86 and 94, to thereby allow a more accurate estimation of the pulsed ion drawout electric field discussed above.

Preferably, computer 38 controls the generation of ions from ion source 74, as will be discussed in greater detail hereinafter, so that computer 38 has knowledge of the times at which ions were introduced into IMS 34, hereinafter referred to as ion introduction events. The computer 38 is then operable to control voltage sources 88 and 96 to repeatedly provide the pulsed ion drawout field some number of times for every ion introduction event. In one embodiment, a pulsed ion drawout field is repeatedly provided 512 times for every ion introduction event. Those skilled in the art will recognize that the number of pulsed ion drawout fields provided for every ion introduction event is directly proportional to the ultimate resolution of the instrument 30. As this pulsed operation relates to some of the advantages of the perpendicular positioning of TOFMS 36 relative to IMS 34, such an arrangement minimizes the possibility that all or part of any one ion packet will travel through the TOFMS 36 unprocessed. Due to the direction of travel of the ion packets relative to the grids or plates 86 and 94, and also to the pulsed nature of the ion drawout electric field, the TOFMS 36 will have multiple chances to accelerate each ion packet toward detector 116 as they travel along axis 72. As such, the instrument 30 is configured to provide for maximum ion throughput to detector 116.

Figure 5:
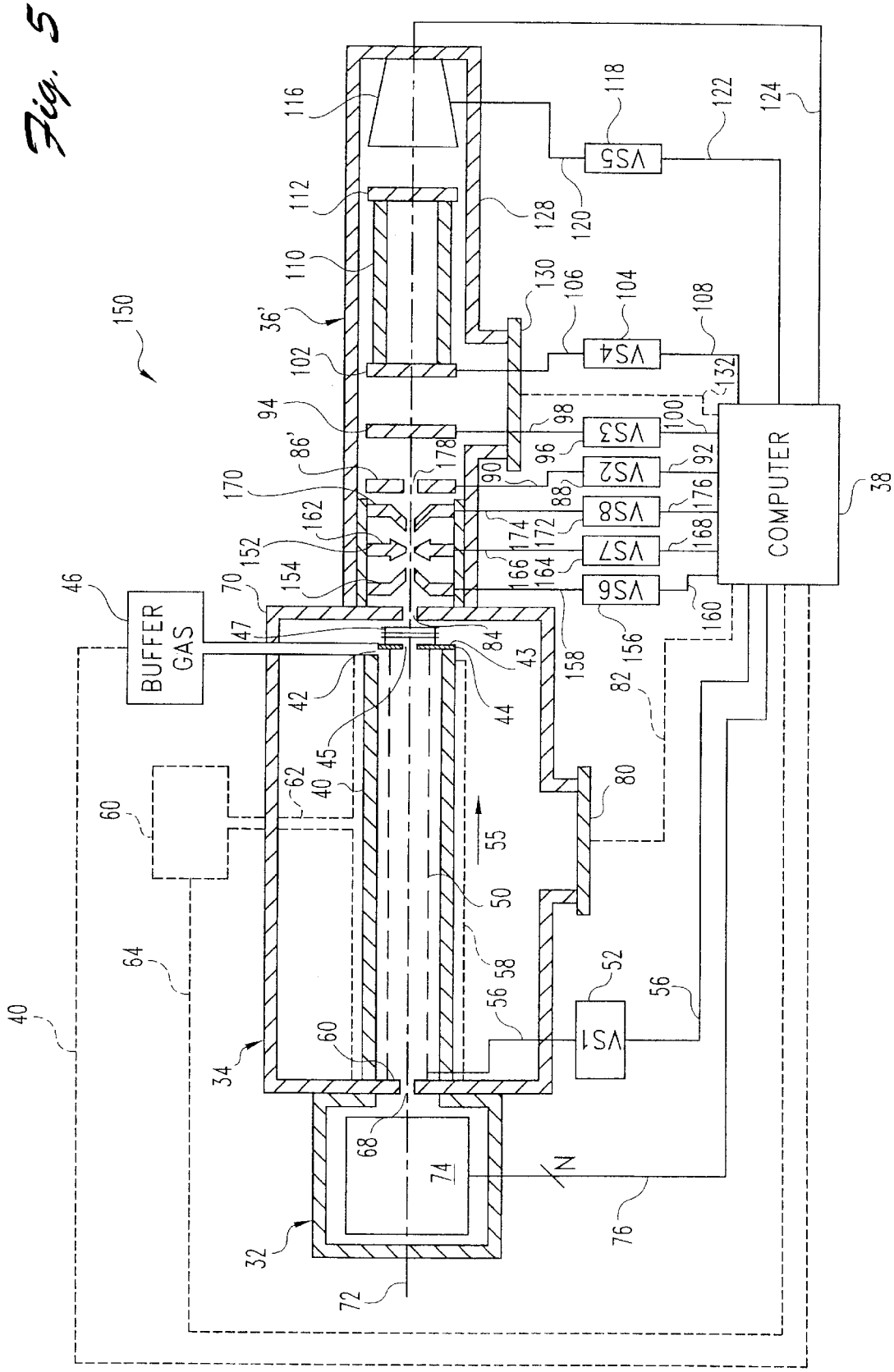
FIG. 5 is a cross-section and schematic diagram of an alternate embodiment of a hybrid ion mobility and time-of-flight mass spectrometer, according to the present invention.

Referring now to FIG. 5, an alternate embodiment of a hybrid ion mobility and time-of-flight mass spectrometer 150, in accordance with the present invention, is shown. Spectrometer 150 is similar in many respects to spectrometer 30 shown in FIG. 4 and described hereinabove, and like components are therefore identified with like numbers. Discussion of the common components, as well as the basic operation of IMS 34 and TOFMS 36', will therefore not be repeated for brevity's sake.

Unlike instrument 30 of FIG. 4, the TOFMS 36' of instrument 150 is positioned relative to IMS 34 such that the drift tube axis 72 also defines the flight tube axis of TOFMS 36'. Alternatively, TOFMS 36' could be arranged relative to IMS 34 with any orientation such that the drift tube axis 72 is non-perpendicular to the flight tube axis. In any such orientation, the initial positions of the ion packets within the space defined between grids or plates 86' and 94 either cannot be estimated with any degree of accuracy (as in the orientation illustrated) or changes as the ion packets travel along axis 72 (as in any non-perpendicular arrangement). Moreover, in any such orientation, it is difficult to estimate when, relative to an ion introduction event, the ion packets will arrive within the space defined between grids or plates 86' and 94, and the timing of the pulsed ion drawout electric fields is thus difficult to predict. As a result, it is likely that the timing of the pulsed ion drawout electric fields will be inaccurate so that ions may be lost within the TOFMS 36' and/or the mass resolution of the TOFMS 36' u will be adversely affected.

In order to address the foregoing problems associated with non-perpendicular positioning of the TOFMS 36' relative to the IMS 34, which are the same problems associated with the Guevremont et al. system discussed hereinabove in the BACKGROUND section, instrument 150 is provided with an ion trap 152 operatively positioned between the ion outlet opening 84 of IMS 34 and the space defined between grids or plates 86' and 94. In the embodiment illustrated in FIG. 5, grid or plate 86' defines an ion inlet opening 178 therethrough which is aligned along axis 72 with ion outlet opening 84 of IMS 34. In other non-perpendicular arrangements of TOFMS 36' relative to IMS 34, ion inlet opening 178 may not be required since ions may enter the space between grids or plates j86' and 94 in the same manner as discussed with respect to the embodiment 30 illustrated in FIG. 4.

In any event, ion trap 152 is preferably a known quadrupole ion trap having a first endcap 154, a center ring 162 and a second endcap 170. Each of the endcaps 154 and 170 define apertures therethrough which align with axis 72. In this configuration, ion trap 152 confines ions therein to a small volume in its center which is in alignment with the ion inlet opening to TOFMS 36'. First endcap 154 is connected to a voltage source VS6 156 via signal path 158, which is itself connected to computer 38 via signal path 160. Center ring 162 is connected to a voltage source VS7 164 via signal path 166, which is itself connected to computer 38 via signal path 168, and second endcap 170 is connected to a voltage source VS8 172 via signal path 174, wherein source 172 is connected to computer 38 via signal path 176. Preferably, sources 156 and 172 are operable to produce DC voltages and source 164 is operable to produce AC voltages in the RF range.

In operation, computer 38 controls sources 156 and 172 to bias endcaps 154 and 170 such that ions exiting ion outlet opening 84 of IMS 34 have just enough energy to enter the opening defined in the first endcap 154. Once therein, the ions collide with buffer gas leaking out of opening 84 into the trap 152, and lose sufficient energy thereby so that the RF voltage on center ring 162 is operable to confine the ions within the trap 152. The confined ions undergo further collisions inside the trap 152 which causes the ions to correspondingly experience further energy loss, resulting in a concentration of the ions toward the center of ring 162 due to the RF voltage thereon. As long as the voltages on endcaps 154 and 170 and center ring 162 are maintained, ions may enter the trap 152 and collect therein. Ions are ejected out of the trap 152 by turning off the RF voltage on center ring 162 and applying an appropriate DC pulse to one of the endcaps 154 or 170. For example, to eject a collection of positively charged ions from trap 152, either the voltage on endcap 154 may be pulsed above that present on endcap 170 or the voltage on endcap 170 may be pulsed below that present on endcap 154. In general, the magnitude of the RF field applied to the center ring via source 164, as well as any DC voltage included therein, may be varied to thereby select ions of any desired mass to charge ratio to be collected by ion trap 152. Ions of all mass to charge ratios, or ions of any particular mass to charge ratio, may be selectively collected within ion trap 152 through proper choice of DC level and RF peak magnitude provided by voltage source 164.

As it relates to the present invention, the ion trap 152 is controllable by computer 38 to periodically eject the collected ion packets therefrom, hereinafter referred to as an ion ejection event, so as to provide for a more accurate estimate of initial ion position within the space defined between grids or plates 86' and 94. Since the computer 38 controls the time at which a packet of collected ions is ejected from ion trap 152, the time at which the ion packet arrives at a specified position in the space defined between grids or plates 86' and 94 can be accurately estimated. Knowing the approximate time, relative to the ion ejection event, at which the ion packet arrives at the specified position between grids or plates 86' and 94, computer 38 may more accurately estimate appropriate timing for applications of the pulsed ion drawout electric field to thereby provide for maximum mass resolution as discussed hereinabove. Moreover, providing for a more accurate estimate of the timing of the pulsed ion drawout electric fields reduces the likelihood that ion packets, or at least portions thereof, will be lost within the TOFMS 36'.

In the operation of instrument 150, IMS 34 is operable to provide packets of ions, which are separated in time as a function of ion mobility, to TOFMS 36' via ion outlet opening 84. Computer 38 controls ion trap 152 to collect the various ion packets therein one at a time, and eject each collected ion packet therefrom at periodic intervals. The ejected ions enter the space defined between grids or plates 86' and 94 as discussed hereinabove, and computer 38 is operable to computer appropriate times at which to apply the pulsed ion drawout electric fields based on the timing of the ion ejection events. The TOFMS 36' is thereafter operable as described hereinabove to produce mass spectrum information.

Figure 3:
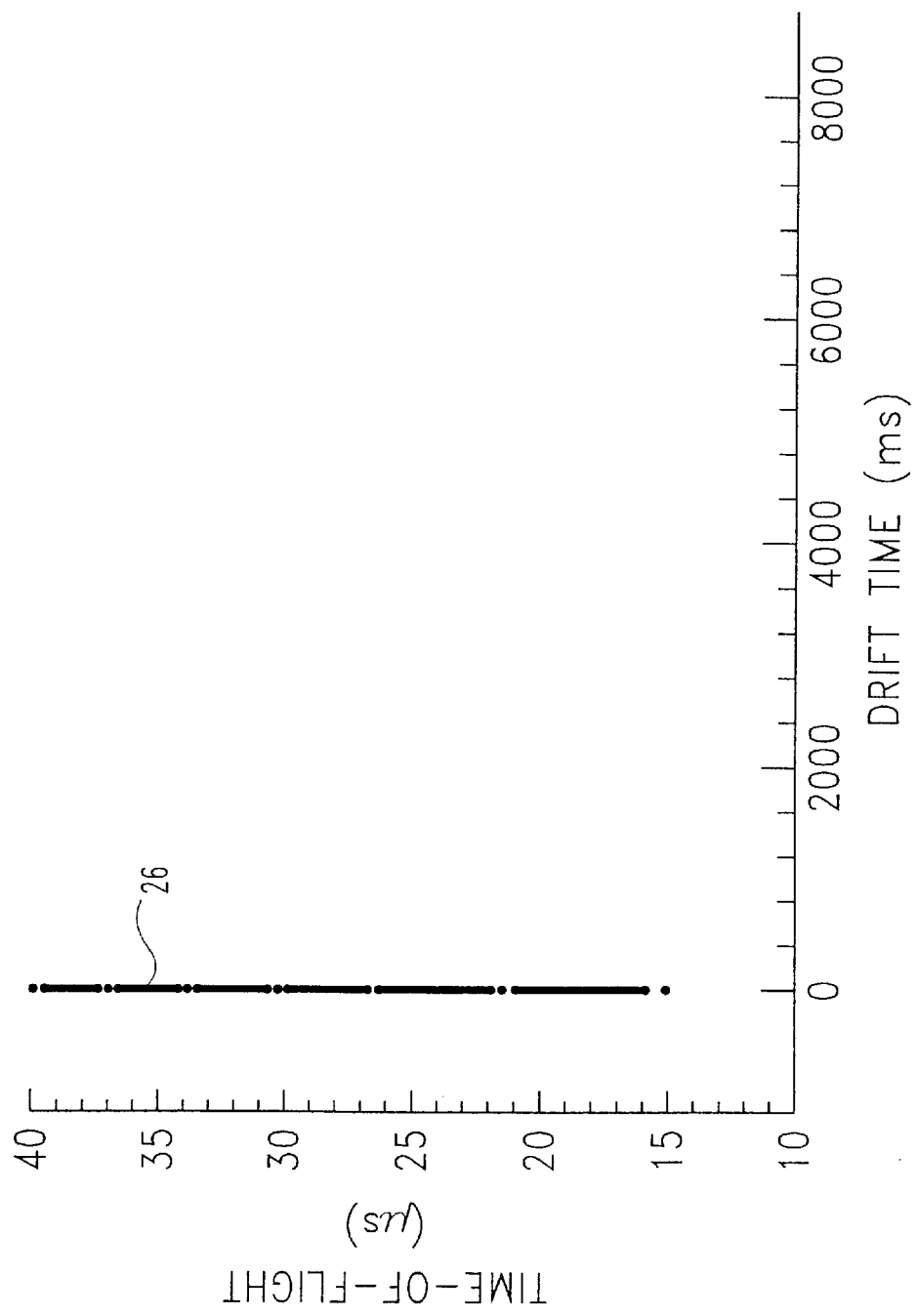
FIG. 3 is a mass spectrum plotted against drift time illustrating the limited resolution of a time-of-flight mass spectrometer.
Figure 6:
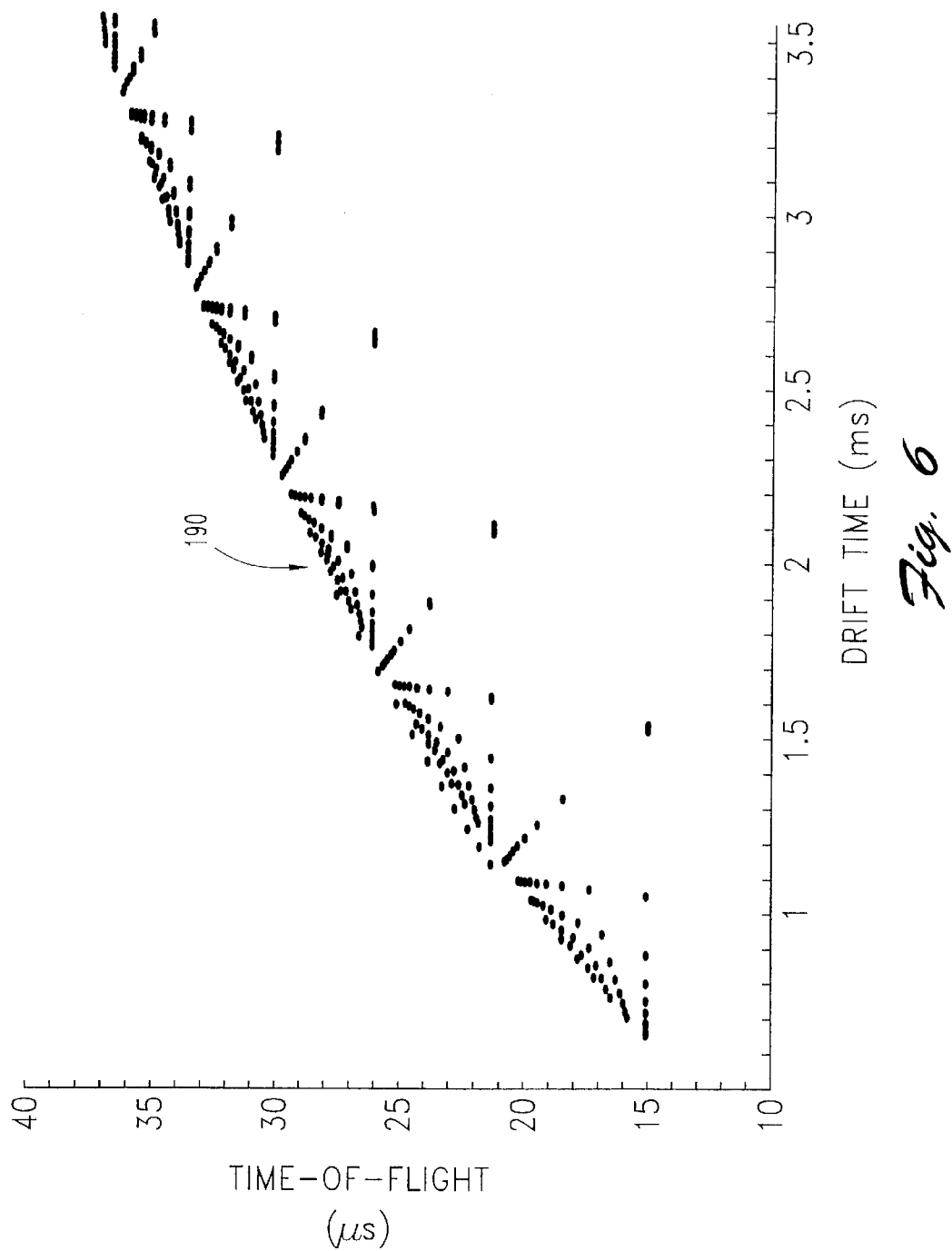
FIG. 6 is a plot of ion time-of-flight vs. ion drift time for oligothymidine, utilizing the hybrid instrumentation of either FIG. 4 or FIG. 5.

Referring now to FIG. 6, a plot 190 of ion flight time vs. ion drift time for an oligothymidine sample is shown, wherein the data shown is producible via either instrument embodiment 30 or 150. As compared to the plot of FIG. 3, it is apparent that the hybrid ion mobility and time-of-flight mass spectrometer of the present invention is operable to resolve structural information of molecules in two substantially orthogonal dimensions. For each drift time, corresponding to arrival in the TOFMS of a corresponding ion packet, the instrument of the present invention is operable to resolve a number of times-of-flight, corresponding to a number of mass to charge ratios. The plot 190 of FIG. 6 thus illustrates that the total resolving power of instrument 30 is drastically better than that achievable via an IMS or TOFMS alone. This technique dramatically reduces the problem of congestion of mass spectra, due to mass peak overlap, in obtaining sequence information for large biomolecules (in excess of 50 residues). The present invention thus provides an instrument for composition, sequence and structural analysis of biomolecules which does not suffer from drawbacks associated with prior art systems discussed in the BACKGROUND section.

Figure 7A:
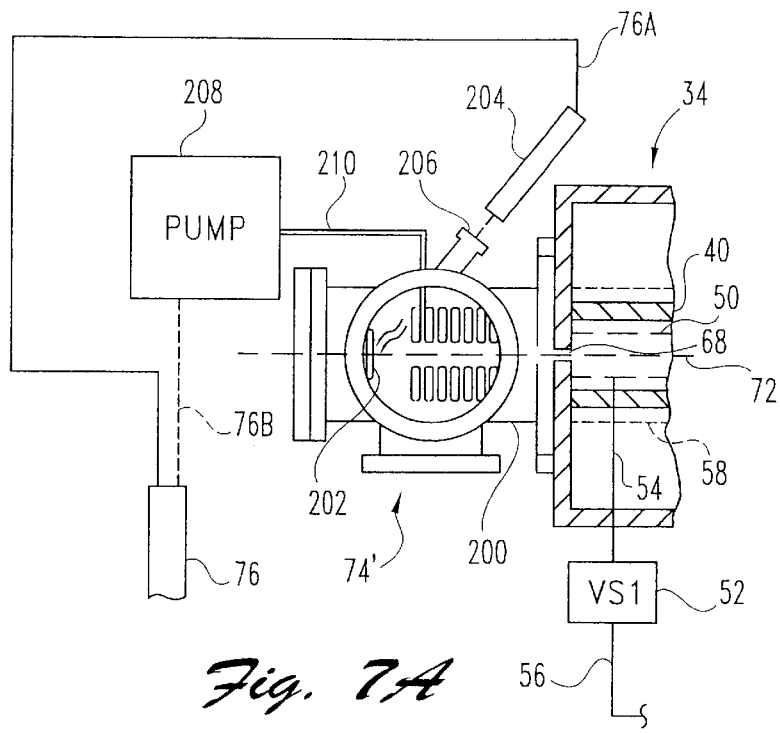
FIG. 7A is a diagrammatic illustration of one preferred embodiment of an ion source for use with any of the instrument configurations shown in FIGS. 4, 5 and 9.

Referring now to FIG. 7A, one preferred embodiment 74' of an ion source 74 for either of the instrument embodiments of FIGS. 4 and 5, is shown. Embodiment 74' includes a chamber 200 having a sample 202 mounted therein and an optical window 206 extending therefrom. A radiation source 204 is electrically connected to computer 38 via signal path 76A, and is configured to direct radiation through optical window 206 to thereby irradiate sample 202. Chamber 200 may include a conduit extending therefrom to a pump 208 which may be controlled by computer 38 via signal path 76B.

Ion source 74' is a known MALDI arrangement wherein radiation source 204, preferably a laser, is operable to desorb gaseous ions from a surface of the sample 202. Computer 38 is operable to control activation times of laser 204 to thereby control sample ionization events. The desorbed ions are directed by the internal structure of chamber 202 to ion inlet opening 68 of IMS 34. The sample 202 may, in accordance with the present invention, be a biomolecule of any size such as DNA, RNA, any of various proteins, carbohydrates, glycoconjugates, and the like. Pump 208 may be controlled to pressurize chamber 208 to thereby conduct high pressure MALDI analysis as is known in the art.

Figure 7C:
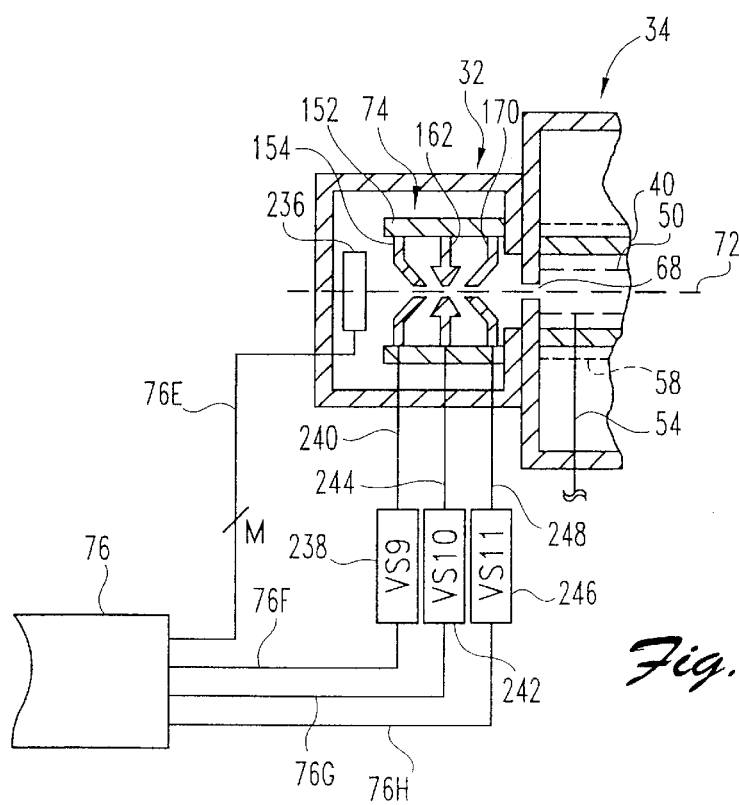
FIG. 7C is a diagrammatic illustration of another alternate embodiment of an ion source for use with any of the instrument configurations shown in FIGS. 4, 5 and 9.
Figure 7B:
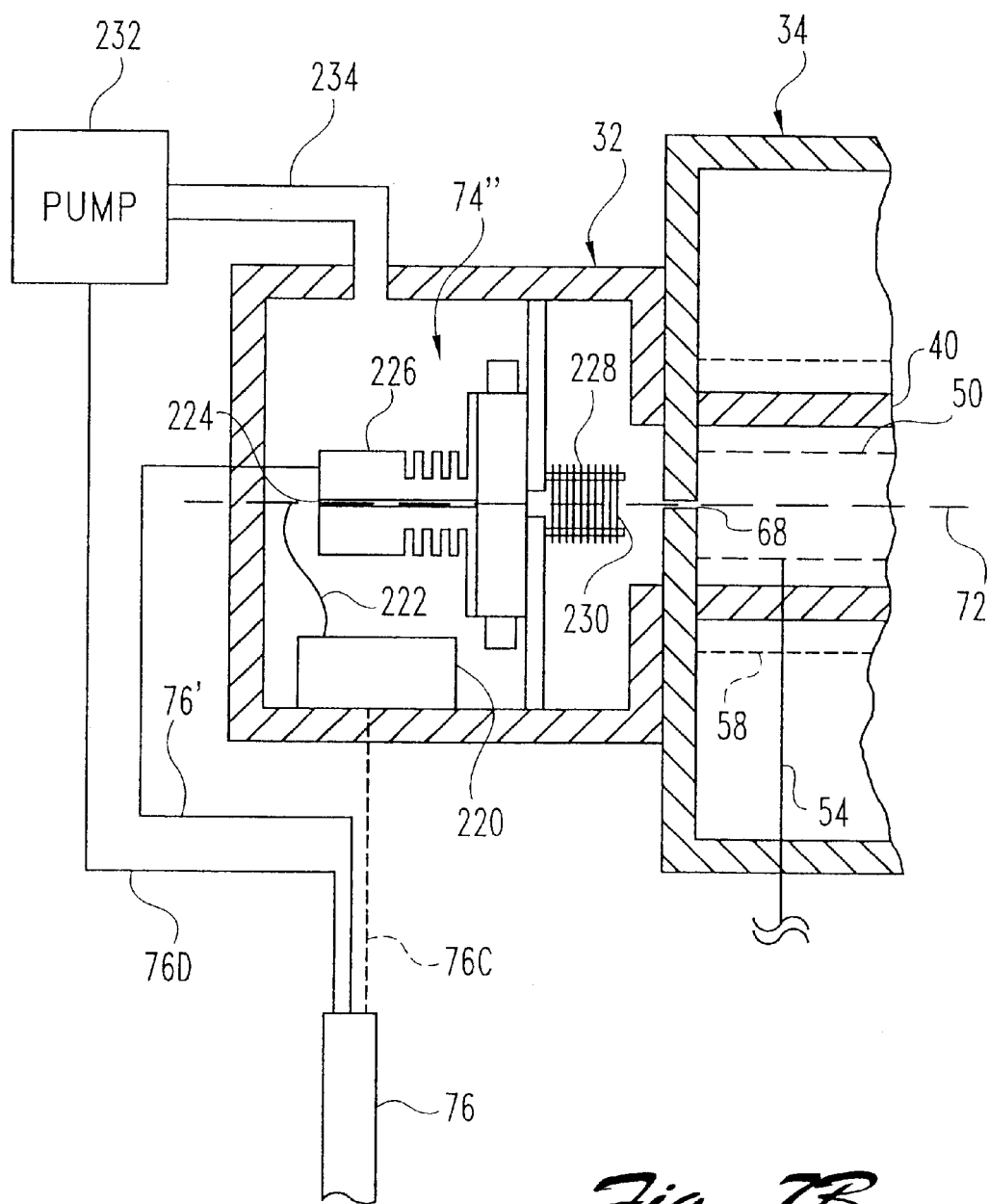
FIG. 7B is a diagrammatic illustration of an alternate embodiment of an ion source for use with any of the instrument configurations shown in FIGS. 4, 5 and 9.

Referring now to FIG. 7B, an alternate embodiment 74" of an ion source 74 for either of the instrument embodiments of FIGS. 4 and 5, is shown. Embodiment 74" includes a liquefied sample 220 having a spray hose or nozzle 222 extending toward an opening defined in a desolvation region 226. Actuation of the spray nozzle 222 may be manually controlled, as is known in the art, or may be controlled by computer 38 via signal path 76C. Desolvation region 226 is connected to computer 38 via signal path 76C', and is operable to convert charged sample droplets supplied thereto via nozzle 222 into gaseous ions and supply these ions to a ion optics member 228. Optics member 230 is operable to focus the gaseous ions and direct them into ion inlet opening of IMS 34. Ion source region 32 includes a conduit extending therefrom to a pump 232 which may be controlled by computer 38 via signal path 76D.

Ion source 74" is a known electrospray ionization (ESI) arrangement operable to convert a liquefied solution containing the sample to gaseous ions. Computer 38 is operable to control activation times of desolvation region 226 to thereby control sample ionization events. Pump 232 is operable to pressurize the ion source region 32 as is known in the art, and the desolvation region 226 is operable convert the liquefied solution to gaseous ions. The sample source 220 may, in accordance with the present invention, include a solution containing a biomolecule of any size such as DNA, RNA, any of various proteins, carbohydrates, glycoconjugates, and the like.

Referring now to FIG. 7C, another alternate embodiment 74''' of an ion source 74 for either of the instrument embodiments of FIGS. 4 and 5, is shown. Embodiment 74''' includes a sample source 236, which may be either of the foregoing sample sources 74' or 74" illustrated in FIG. 7A or 7B, and which may be controlled as described hereinabove by computer 38 via a number, M, of signal paths 76E, wherein M may be any integer less than N (see FIGS. 4 and 5).

Ion source 74''' further includes an ion trap 152 positioned between ion source 236 and the ion inlet opening 68 of IMS 34. Ion trap 152 is preferably a known quadrupole ion trap identical to that shown in FIG. 5 and described hereinabove. A detailed discussion of the operation of ion trap 152 therefore need not be repeated here. Endcap 154 is connected to a voltage source VS9 238 via signal path 240, center ring 162 is connected to a voltage source VS10 242 via signal path 244 and endcap 170 is connected to a voltage source VS11 246 via signal path 248. VS9, VS10 and VS11 are each connected to computer 38 via signal paths 76F, 76G and 76H, respectively. Computer 38 is operable to control VS9, VS10 and VS11 identically as described with respect to VS6, VS7 and VS8, respectively, of FIG. 5.

In operation, computer 38 is operable to control ion trap 152, in a manner similar to that described hereinabove, to collect a bulk of ions therein and selectively eject the collected ions therefrom toward ion inlet opening 68 of IMS 34. As is known in the art, the peak resolution of an ion mobility instrument, such IMS 34, is limited by the length of the input pulse of ions into the instrument. Generally, mobility peaks cannot be resolved any better than the time length of the input ion pulse. A drawback particularly associated with the use of ESI is that the input ion pulse width must typically be at least 50 $\mu$s in order to produce enough ions for analysis. However, with the ion source arrangement 74''' shown in FIG. 7C, computer 38 is operable to collect a large number of ions within ion trap 152 prior to pulsing the ions into the IMS 34. With a sufficient number of ions collected in ion trap 34, the only limitation on the ion input pulse length, and hence the resolution capability of IMS 34, is the time required to open and close ion trap 152. With existing ion traps, the ion input pulse lengths may be reduced to less than 1.0 $\mu$s in duration.

Figure 8B:
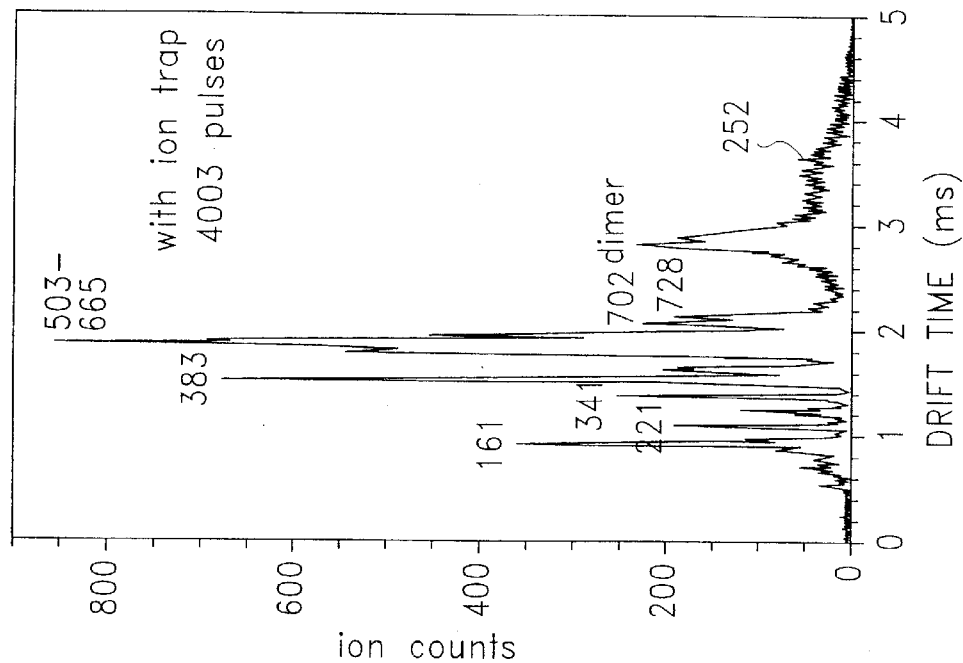
FIG. 8B is a plot of ion intensity vs. ion drift time for an IMS instrument having an ion trap disposed between the ion source and the IMS instrument.
Figure 8A:
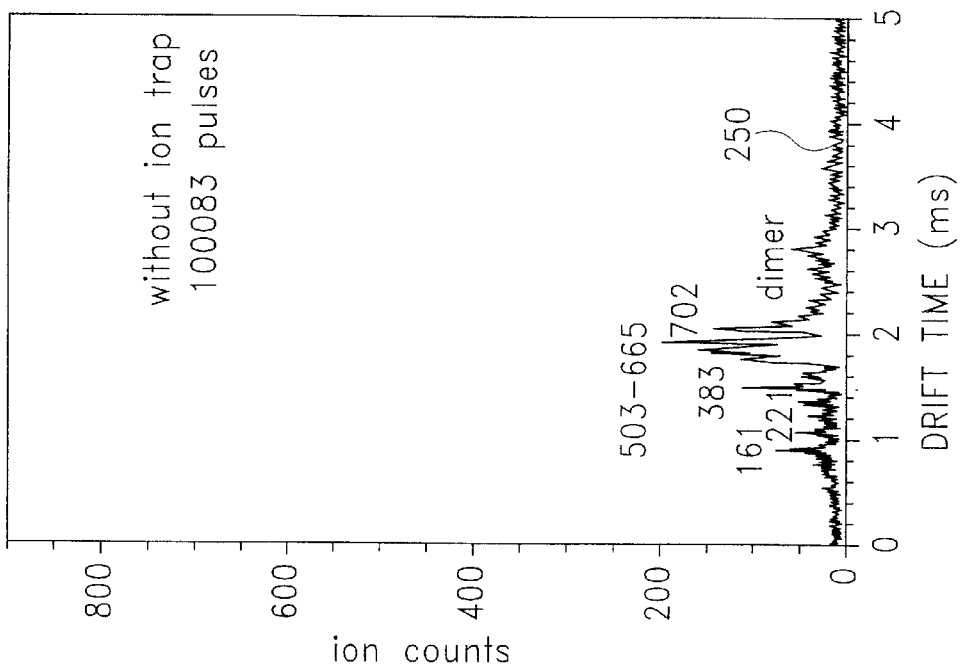
FIG. 8A is a plot of ion intensity vs. ion drift time for an IMS instrument without an ion trap disposed between the ion source and the IMS instrument.

FIGS. 8A and 8B show a comparison of ion mobility distributions for a maltotetraose sample, wherein the spectrum 250 of FIG. 8A was produced using an ESI source similar to that shown in FIG. 7B, with 100,083 input pulses of 20 $\mu$s duration. The spectrum 252 of FIG. 8B was produced using the same ESI source as that used for FIG. 8A along with an ion trap, such as ion trap 152 shown in FIG. 7C, with 4003 pulses of 1 $\mu$s duration. Compared to spectrum 250, spectrum 252 has a 4–5 times increase in signal strength, an increase in resolution by a factor of approximately 20 and an increase in signal-to-noise ratio by a factor of approximately 20 as well.

Referring again to FIG. 7C, ion trap 152 may be used with any known ion generation source to increase not only the resolution and sensitivity of IMS 34 along, but also the resolution and sensitivity of either hybrid instrument 30 or 150 of FIGS. 4 and 5.

It is to be understood that either embodiment of the hybrid ion mobility and time-of-flight mass spectrometer shown and described herein is capable of operation in a number of different operational modes. For example, the structure and operation of the various embodiments of the present invention have been described herein according to a first mode of operation wherein ions of relatively low energy are generated and injected into the hybrid instrument, from which structural information relating to the ions can be obtained.

In a second mode of operation, such ions could be injected into the hybrid instrument at higher energies, wherein high energy collisions with the buffer gas within the IMS 34 result in ion fragmentation. In such a case, the ion fragments, separated in time as a function of their mobilities, would be supplied to the TOFMS portion of the instrument, wherein mass spectra information of the various fragments could be obtained for sequencing analysis. Alternatively, fragmentation of ions for such analysis may be accomplished via any of a number of other known techniques. Examples of such known alternative ion fragmentation techniques include enzyme degradation fragmentation, photo-fragmentation, thermal dissociation such as by heating drift tube 40 via control of variable temperature source 60, electron impact dissociation, surface induced dissociation, and blackbody infrared radiation induced dissociation.

In a third mode of operation, ions of only a particular mass could be processed by the hybrid instrument. One way of generating ions of only a particular mass is to adjust the peak amplitude and/or DC voltage of the center ring voltage source of an ion trap positioned prior to the IMS 34. By properly adjusting this voltage, ion trap 152 may be configured to store therein only ions having a particular mass to charge ratio. In this manner, the ion trap 152 is controlled to act as an ion filter. Another way of analyzing ions of only a particular mass is to provide an ion trap 152 between the IMS 34 and TOFMS 36, and controlling the ion trap 152 as just discussed to filter out ions having undesirable mass to charge ratios.

In a fourth mode of operation, high energy ions of only a particular mass are introduced into the IMS 34. Therein, these ions undergo fragmentation, and such fragments could then be further processed by the TOFMS 36 as discussed above.

Referring now to FIG. 9, one preferred embodiment of an ion mobility and mass spectrometer instrument 300 that is particularly well suited for conducting sequencing analysis in a manner similar to that just described hereinabove with respect to the second mode of operation, in accordance with the present invention, is shown. Several of the components of instrument 300 are identical to those shown and described with respect to FIGS. 4 and 5, and some of the structural and operational details thereof will accordingly be omitted here for brevity. For example, instrument 300 includes an ion source 32 operatively connected to an ion mobility spectrometer (IMS), wherein IMS 34 includes a source of buffer gas 46 that is controllable via operation of a pump 80 as described hereinabove. Instrument 300 further includes a mass spectrometer (MS) 36, preferably a time-of-flight mass spectrometer (TOFMS), that is configured to receive ions from IMS 34 as described hereinabove. In this embodiment, however, the drift tube axis of IMS 34 (not shown in FIG. 9) and the flight tube axis of TOFMS 36 (not shown in FIG. 9) may be arranged at any desired angle with respect to each other. It has been determined through experimentation that for non-perpendicular configurations of IMS 34 relative to TOFMS 36 (i.e., configurations other than that illustrated in FIG. 4), an ion trap 152 (see FIG. 5) is not required as described hereinabove if the ion acceleration region (between grids 86, 94 and 102) of TOFMS 36 is continually activated or pulsed. In other words, ions need not be collected in an ion trap 152 for timing purposes if the ion acceleration region of TOFMS 36 is continually pulsed in a free-running operational mode. Accordingly, ion trap 152 may be omitted from any perpendicular or non-perpendicular configurations of the IMS drift tube axis relative to the TOFMS flight tube axis, although the present invention contemplates that such an ion trap 152 may optionally be used in such configurations as desired, wherein trap 152 may be positioned adjacent to the entrance of TOFMS 36.

Instrument 300 further includes a computer 310 having a memory 312. Computer 310 is preferably operable to control the flow rate of buffer gas #1 within buffer gas source 46 via signal path 48, and is further preferably operable to control pump 80 of IMS 34 via signal path 82 and a vacuum pump 130 of TOFMS 36 via signal path 132, as described hereinabove. Computer 310 is also operable to control ion source 32 via a number, N, of signal paths 76, wherein N may be any integer, and is further operable to receive ion detection signals from TOFMS 36 via signal path 124 and process such signals to produce two-dimensional ion spectra; e.g. ion mass vs. ion mobility, as described hereinabove.

Instrument 300 includes a number, J, of voltage sources $314_1$–$314_J$ connected to computer 310 via signal paths $316_1$–$316_J$. Voltage sources $314_1$–$314_J$ are operatively connected to IMS 34 via corresponding signal paths $318_1$–$318_J$. In operation, computer 310 is operable to control voltage sources $314_1$–$314_J$ to thereby control the operation of IMS 34 as described hereinabove. Instrument 300 further includes another number, M, of voltage sources $330_1$–$330_M$ connected to computer 310 via signal paths $332_1$–$332_M$. Voltage sources $330_1$–$330_M$ are operatively connected to TOFMS 36 via corresponding signal paths $334_1$–$334_M$. In operation, computer 310 is operable to control voltage sources $330_1$–$330_M$ to thereby control the operation of TOFMS 36 as described hereinabove.

The components of instrument 300 described thus far with respect to FIG. 9 are identical to previously described components of the instruments 30 and/or 150 of FIGS. 4 and 5. Unlike instruments 30 and 150, however, instrument 300 further includes a quadrupole mass filter 302 having an ion inlet coupled to the ion outlet of IMS 34 and an ion outlet coupled to an ion inlet of a collision cell 304 of known construction. An ion outlet of collision cell 304 is coupled to an ion inlet of TOFMS 36; i.e., to the ion acceleration region defined between plates or grids 86 and 94 of TOFMS as shown in FIGS. 4 and 5. Collision cell 304 includes a source of buffer gas 306, wherein the flow rate of buffer gas #2 is controlled by computer 310 via signal path 307, preferably in a manner described hereinabove with respect to the computer control of the buffer gas source 46 of FIG. 4. Alternatively, buffer gas source 306 may be omitted and buffer gas source 46 may be configured to provide buffer gas #1 to cell 304 via conduit 305 as shown in phantom in FIG. 9. Collision cell 304 further includes a pump 308 of known construction, the operation of which is controlled by computer 310 via signal path 309. As is known in the art, pump 308 may be controlled to establish and maintain a desired quantity of buffer gas within collision cell 304, and may further be controlled to purge cell 304 of buffer gas. Alternatively, structure 308 may represent a manually actuatable or computer controlled valve. In this case, valve 308 may be controlled to establish and maintain a desired quantity of buffer gas #2 within collision cell 304, or may alternatively be controlled to establish and maintain a desired quantity of buffer gas #1 within the quadrupole mass filter 302 and collision cell 304.

A number, K, of voltage sources $320_1$–$320_K$ are provided, wherein K may be any integer, and wherein control inputs of sources $320_1$–$320_K$ are connected to computer 310 via corresponding signal paths $322_1$–$322_K$. Outputs of voltage sources $320_1$–$320_K$ are operatively connected to the quadrupole mass filter (QMF) 302, in a manner to be described more fully hereinafter with respect to FIGS. 11 and 12, via corresponding signal paths $324_1$–$324_K$. A number, L, of voltage sources $326_1$–$326_L$ are provided, wherein L may be any integer, and wherein control inputs of sources $326_1$–$326_L$ are connected to computer 310 via corresponding signal paths $328_1$–$328_L$. Outputs of voltage sources $326_1$–$326_L$ are operatively connected to the collision cell 304 in a known manner via corresponding signal paths $329_1$–$329_L$.

Figure 10:
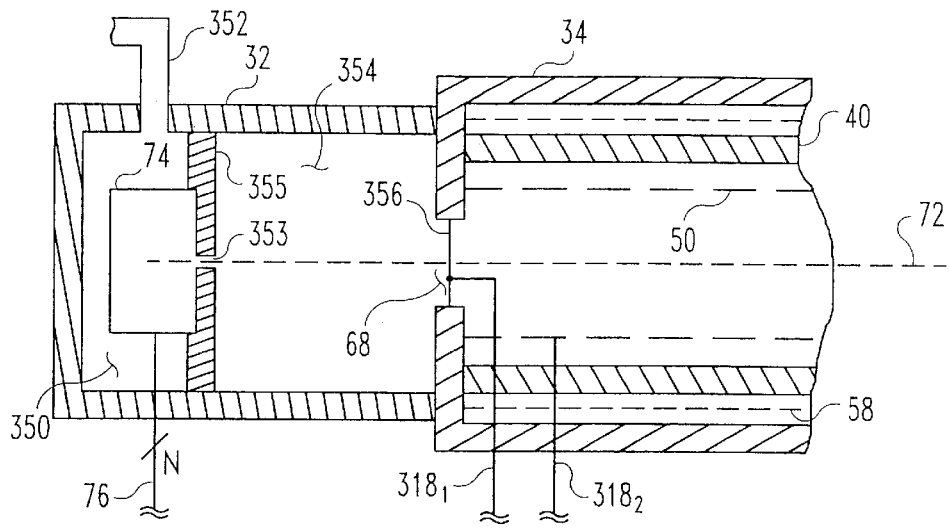
FIG. 10 is a partial cross-sectional diagram of yet another alternate embodiment of an ion source for use with any of the instrument configurations shown in FIGS. 4, 5 and 9.

Referring now to FIG. 10, a cross-section of another preferred structure of the ion source 32 for use with any of the instruments illustrated in FIGS. 4, 5 and 9, in accordance with the present invention, is shown. Ion source 32 includes an ion source chamber 350 separated from an ion collection chamber 354 by a wall or partition 355. Ion source chamber 350 includes a port having a conduit 352 connected thereto, wherein conduit 352 is preferably connected to a pump or valve of known construction for changing gas pressure within region 350. An ion source 74 is disposed within region 350, wherein source 74 may be any of the ion sources 74', 74" or 74''' described hereinabove with respect to FIGS. 7A–7C, and/or any combination thereof. Wall or partition 355 includes an aperture 353 therethrough that is aligned with an ion outlet of ion source 74 and is also preferably aligned with a longitudinal axis of the drift tube 40 of IMS 34, wherein aperture 353 defines an ion inlet to ion collection chamber 354. An electrically conductive grid, or series of vertically or horizontally parallel wires, 356 (hereinafter "grid") is positioned across the ion inlet aperture 68 of IMS 34, wherein grid 356 is connected to one of the voltage sources $314_1$ via signal path $318_1$. Computer 310 is operable to control the voltage of grid 356, as is known in the art, to thereby permit and inhibit entrance of ions into IMS 34. For example, computer 310 is operable to inhibit entrance of ions into IMS 34 by activating voltage source $314_1$ to thereby cause ions in the vicinity of grid 356 to be attracted thereto and neutralized upon contact. Conversely, computer 310 is operable to permit entrance of ions into IMS 34 by deactivating voltage source $314_1$ to thereby permit passage of ions therethrough. Alternatively, the ion gating function may be accomplished by a voltage source $320_2$ connected to guard rings 50 via signal path $318_2$, wherein computer 310 is operable to control source $320_2$ to attract ions to guard rings 50 when it is desirable to inhibit ions from traveling through drift tube 40. In this case, grid 356 and voltage source $320_1$ may be omitted from FIG. 10. Alternatively still, the ion gating function may be accomplished by impressing a voltage across aperture 68 to thereby create an electric field therebetween. In this case, computer 310 is operable to control the voltage across aperture 68 to divert ions toward guard rings 50 when it is desirable to inhibit ions from traveling through drift tube 40. Those skilled in the art will recognize that any known technique for pulsing ions from ion collection chamber 354 through ion inlet aperture 68, including for example any known electrical, mechanical and/or electromechanical means, may be used, and that any such technique falls within the scope of the present invention.

In any case, the ion collection chamber 354 is functionally similar to the ion trap 152 of FIG. 7C in that it provides for the collection of a large quantity of ions generated by ion source 74 prior to entrance into IMS 34. Through appropriate control of ion source 74 and grid 356 or equivalent, the quantity of ions entering IMS 34 may thus be correspondingly controlled.

Figure 11:
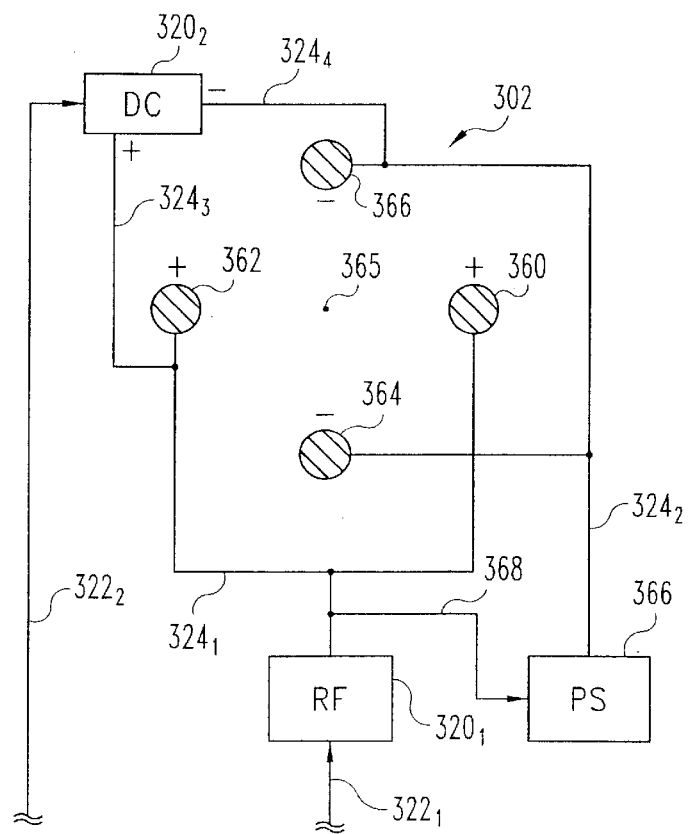
FIG. 11 is a cross-section of one preferred embodiment of the quadrupole mass filter illustrated in FIG. 9 as viewed along section lines 11—11.

Referring now to FIG. 11, a cross-section of the quadrupole mass filter (QMF) 302, as viewed along section lines 11—11 of FIG. 9, is shown. QMF 302 includes four electrically conductive rods or plates 360, 362, 364 and 366 that are preferably disposed equidistant from a longitudinal axis 365 extending through QMF 302. Two of the opposing rods 360 and 362 are electrically connected to voltage source $320_1$ via signal path $324_1$, wherein source $320_1$ has a control input connected to computer 310 via signal path $322_1$. Signal path $324_1$ is connected to a signal phase shifter 366 of known construction via signal path 368, wherein a signal output of phase shifter 366 is electrically connected to the remaining two opposing rods 364 and 366. Computer 310 is operable to control voltage supply $320_1$, which is preferably a radio frequency (RF) voltage source, to thereby control the RF voltage applied to rods 360 and 362. Phase shifter 366 is preferably operable to shift the phase of the RF voltage on signal path 368 by 180° and apply this phase shifted RF voltage to signal path $324_2$. Those skilled in the art will recognize that phase shifter 366 may alternatively be replaced with a second RF voltage source that is controllable by computer 310 to produce an RF voltage identical to that produced by source $320_1$ except shifted in phase by 180°. In any case, signal paths $324_1$ and $324_2$ are electrically connected to voltage source $320_2$ via signal paths $324_3$ and $324_4$ respectively, wherein source $320_2$ has a control input connected to computer 310 via signal path $322_2$. Voltage source $320_2$ is preferably a DC voltage supply controllable by computer 310 to thereby impress a DC voltage between rod pairs 360/362 and 364/366.

Figure 12:
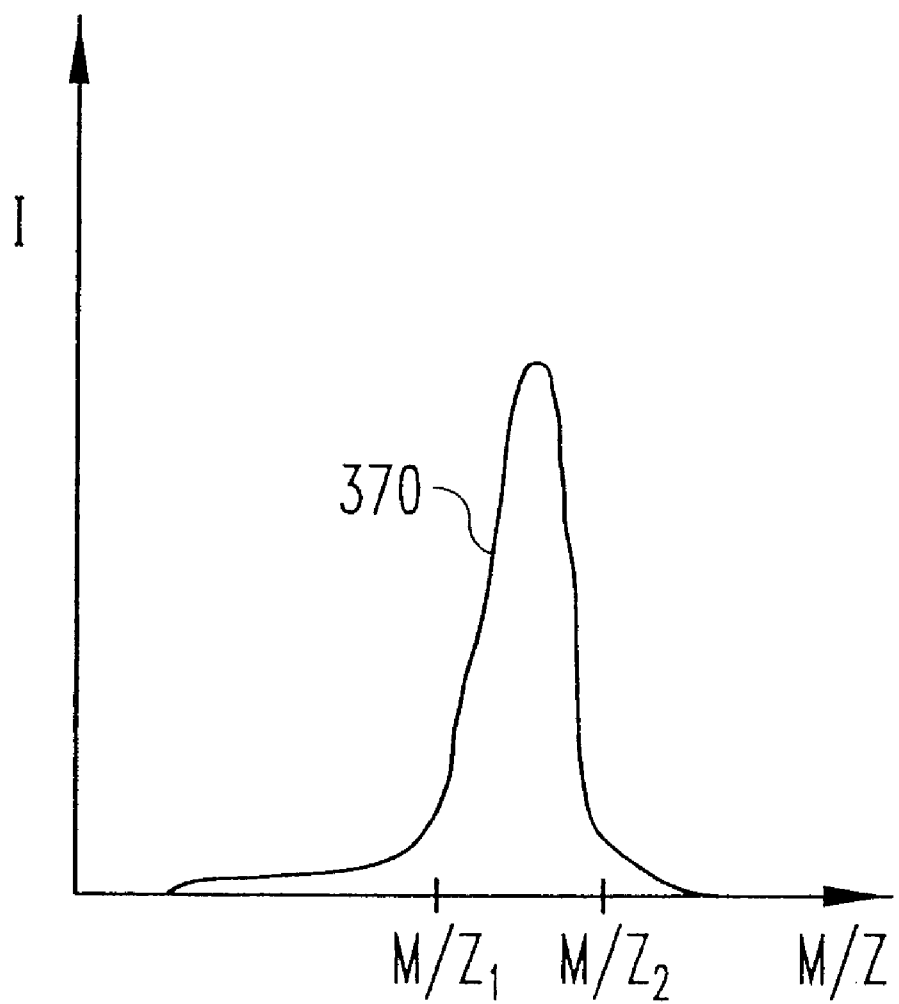
FIG. 12 is a plot of ion intensity vs. mass-to-charge ratio illustrating operation of the quadrupole mass filter of FIG. 11.

In the operation of QMF 302, the RF voltages applied to rods 360–366 alternately attract ions to rod pairs 360/362 and 364/366, wherein this attraction increases with decreasing ion mass-to-charge ratio (m/z). Below some threshold m/z value (i.e., lighter ions), the ions come into contact with one of the rods 360–366 and are accordingly neutralized or ejected. The m/z value below which ions are neutralized is determined by the strength and frequency of the RF signal as is known in the art. The DC voltage applied to rods 360–366 similarly attracts ions thereto wherein this attraction increases with increasing m/z values. Above some threshold m/z value (i.e., heavier ions), the ions come into contact with one of the rods 360–366 and are accordingly neutralized. The m/z value above which ions are neutralized is determined by the strength of the DC signal as is known in the art. Referring to FIG. 12, a plot 370 of ion intensity at the ion outlet of QMF 302 is shown demonstrating that the RF and DC voltages applied to rods 360–366 result in passage through QMF 302 only of ions having m/z values above a minimum m/z value m/$z_1$ and below a maximum m/z value m/$z_2$. QMF 302 thus acts as a bandpass filter wherein the pass band of m/z values is controlled via computer 310 by controlling the operating strength and frequency of the RF voltage supply $320_1$ and by controlling the operating strength of the DC voltage supply $320_2$. In accordance with an important aspect of the present invention, computer 310 is operable, under certain operating conditions, to control the m/z values of ions being passed from IMS 34 to the collision cell 304 as will be descried in greater detail hereinafter.

The collision cell 304 is of known construction, and the filling and purging of buffer gas therein/therefrom is preferably controlled by computer 310 in a known manner. Alternatively, the filling and purging of cell 304 may be manually controlled via known means. In either case, when cell 304 is filled with buffer gas, ions provided thereto by QMF 302 undergo collisions with the buffer gas and fragmentation of parent ions into a number of daughter ions results as is known in the art. In a preferred embodiment, the internal structure of the collision cell 304 is similar to that of the quadrupole mass filter illustrated in FIG. 11 except that collision cell 304 includes eight rods (poles) rather than four, and is accordingly referred to as an octopole collision cell. At least one of the voltage sources $326_1$–$326_L$ is preferably a RF voltage source connected between two pairs of four opposing poles, wherein computer 310 is operable to control the RF voltage source to thereby concentrate ions centrally therein and provide a low-loss channel or pipe between QMF 302 and MS 36. The buffer gas for cell 304 may be, for example, Argon, Helium or Xenon, although the present invention contemplates using other gases provided to cell 304 via source 306 or 46 as described hereinabove. The present invention contemplates that collision cell 304 may alternatively be configured in accordance with any desired trapping multiple (e.g., quadrupole, hexapole, etc.). Alternatively still, collision cell 304 may me configured as a non-trapping gas collision cell. In any event, those skilled in the art will recognize that the importance of any such collision cell arrangement lies in its ability to provide for fragmentation of entering parent ions into daughter ions.

Figure 13:
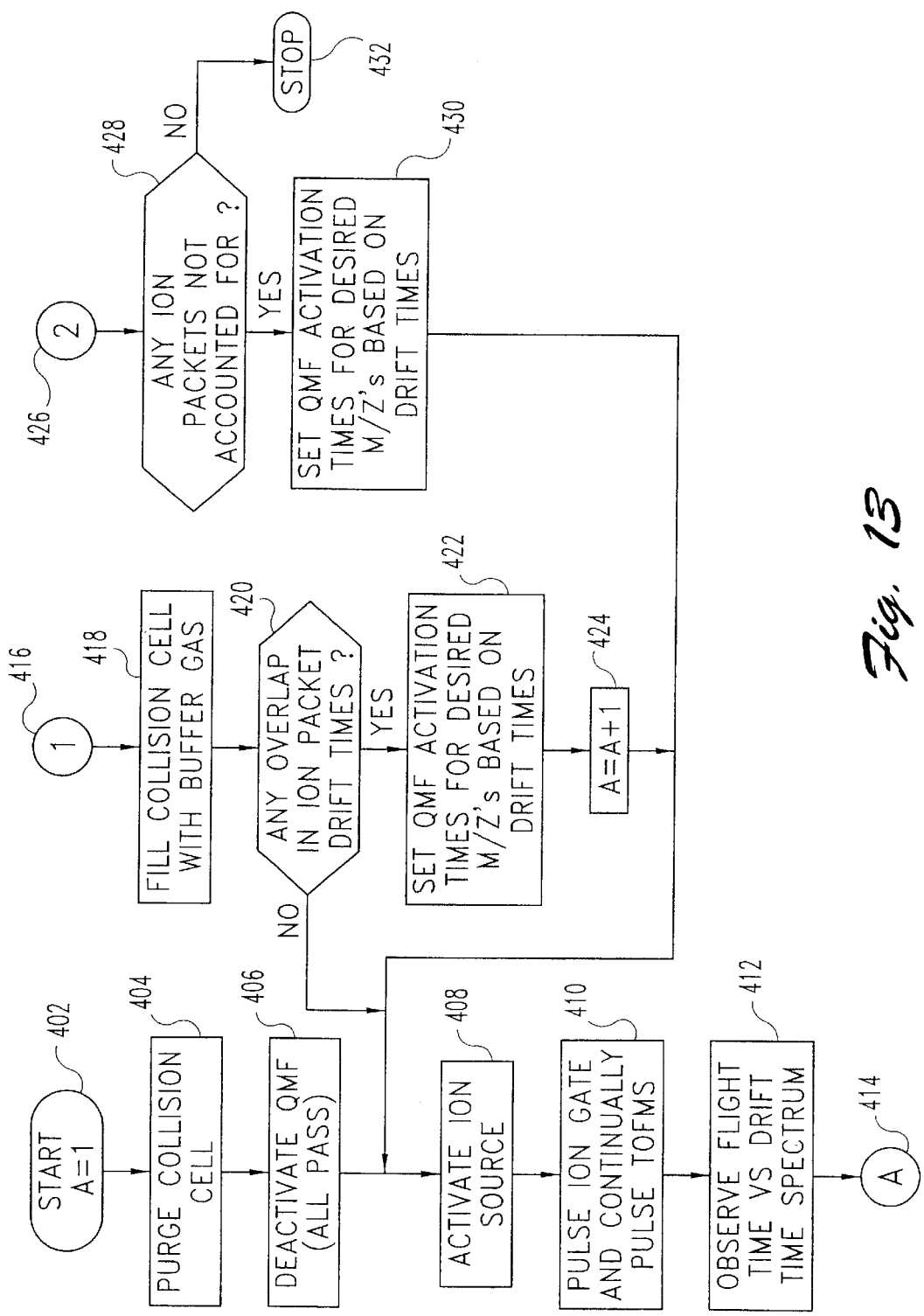
FIG. 13 is a flowchart illustrating one preferred embodiment of a process for conducting sequencing analysis using the instrument configuration of FIG. 9, in accordance with the present invention.

Referring now to FIG. 13, one preferred embodiment of a process 400 for conducting sequencing analysis using the instrument 300 illustrated in FIG. 9, in accordance with the present invention, is shown. Process 400 begins at step 402 where a counter variable A is set equal to an arbitrary initial number (e.g., 1). Thereafter at step 404, collision cell 304 is purged of buffer gas either manually or under the control of computer 310 in a known manner. It is to be understood, however, that if no buffer gas initially exists in cell 304, step 404 may be avoided. Thereafter at step 406, computer 310 is operable to control QMF 302 so as to. pass ions having any m/z value therethrough. In one embodiment, computer 310 is operable to execute step 406 by deactivating voltage sources $320_1$ and $320_2$ to thereby operate QMF 302 in an all-pass operational mode; i.e., such that QMF 302 passes ions having all m/z values therethrough.

Process 400 continues from step 406 at step 408 where computer 310 is operable to activate ion source 74 to thereby begin the generation of ions from a suitable sample source. Thereafter at step 410, control computer 310 is operable to pulse ion gate 356 (FIG. 10) for a predetermined duration to thereby permit entrance of a gaseous bulk of ions from collection chamber 354 into IMS 34, and to continually pulse the ion acceleration region of MS 36, as described hereinabove, to thereby operate MS 36 in a free running mode. Those skilled in the art will recognize that when using embodiments of ion source 32 other than that shown in FIG. 10 (e.g., those of FIGS. 7A and 7B), steps 408 and 410 may be combined such that computer 310 is operable to activate the ion source and supply a gaseous bulk of ions to IMS 34 in a single step. In any case, process 400 continues from step 410 at step 412 where a spectrum of ion flight times (i.e., ion mass) vs. ion drift times (i.e., ion mobilities) resulting from passage of ions through IMS 34 and MS 36, as described hereinabove, is observed.

Referring now to FIGS. 14A–14D, a graphical example of steps 410 and 412 is illustrated. Signal 450 of FIG. 14A represents the voltage at ion gate 356, wherein computer 310 is operable to pulse gate 356 to an inactive state for a predetermined duration at step 410 to thereby permit entrance of a bulk of gaseous ions into IMS 34. Signal 452 of FIG. 14B represents the voltage at the ion acceleration region of TOFMS 36, wherein computer 310 is operable to pulse the ion acceleration region in a free running manner at step 410 to thereby periodically accelerate ions or parts of ions toward the ion detector. A typical value for the duration of deactivation of ion gate signal 450 is 100 µs, a typical value for the duration of activation of the TOFMS signal 452 is 3 µs, and a typical value for the time between TOFMS signal activation is 100 µs. However, the present invention contemplates other values for the foregoing signal durations, and it will be understood that the actual signal durations used will typically be dictated by many factors including sample type, analysis mode, information sought and the like. In any case, signal 454 of FIG. 14C represents the activation state of QMF 302, wherein computer 310 is operable throughout steps 410 and 412 to maintain QMF 302 in an inactive or all-pass state; i.e. QMF 302 is operable to pass ions having any m/z value therethrough. Finally, a spectrum 456 of ion drift time (corresponding to ion mobility) vs. ion flight time (corresponding to ion mass) is shown in FIG. 14D illustrating one example of the resulting ion spectrum of step 412.

Close inspection of spectrum 456 of FIG. 14D reveals that ions a, b and g do not overlap in drift times with any other ion, while ions c and d and ions e and f overlap in their respective drift times. Ions c and d will accordingly arrive at collision cell 304 at approximately the same time (3.5 µs), and ions e and f will accordingly arrive at collision cell 304 at approximately the same time (4.8 µs). If collision cell 304 was filled with buffer gas so that ion fragmentation occurred, TOFMS 36 would not be able to accurately distinguish parent and daughter ions attributable to ion c from those of ion d and likewise those attributable to ion e from those of ion f. If, however, no such overlaps occurred, the foregoing problem would not occur. In accordance with an important aspect of the present invention, process 400 is configured to conduct subsequent sequencing analysis (via fragmentation) with QMF 302 operating in an all-pass mode if no overlap in ion drift times are evident from step 412, but is alternatively operable to conduct subsequent sequencing analysis (via fragmentation) with QMF 302 operable to selectively filter out all but one of the ions overlapping in any one drift time. In the latter case, the sequencing analysis is repeated until fragmentation spectra are produced for all ions in the original spectrum (FIG. 14D). Thus in the example of FIG. 14D, sequencing analysis is conducted by filling collision cell 304 with buffer gas and operating QMF 302 to selectively filter out ions d and f, for example, such that the resulting fragmentation spectrum includes fragmentation spectra of ions a, b, c, e and g. The sequencing analysis is repeated by controlling QMF 302 to selectively filter out ions c and e such that the resulting fragmentation spectrum includes fragmentation spectra of at least ions d and f. In general, the instrument 300 must be taken through an ion generation/resulting spectrum sequence Z+1 times for any sample, wherein Z is the maximum number of ions overlapping in drift time and the "1" accounts for the initial operation of instrument 300 in order to produce the spectrum 456 of FIG. 14D. In the example illustrated in FIGS. 14, 15 and 16, instrument 300 must accordingly be taken through the ion generation/resulting spectrum sequence three times since the maximum number of ions overlapping in drift time is two (e.g., two ions c and d overlap in drift time and, two ions f and e overlap in drift time).

Referring again to FIG. 13, process 400 continues from step 412 and step 414 where process 400 is directed to the subprocess flagged with the current value of A. In the first time through process 400, A=1 so process 400 jumps to step 416. Thereafter at step 418, the collision cell 304 is filled with buffer gas from buffer gas source 306 (or buffer gas source 46). As with step 404, step 418 may be executed manually or under the control of computer 310. In either case, process 420 advances from step 418 to step 420 where a determination is made as to whether there exists any overlap in ion packet drift times. Step 420 is preferably carried out by manually observing spectrum 456 (FIG. 14D), although the present invention contemplates that step 420 may be automated in accordance with known techniques and therefore executed by computer 310. In either case, if no overlap in ion drift times are present in the spectrum resulting at step 412, steps 408–412 are repeated and a spectrum of fragmented parent and daughter ions results, wherein the spectrum of fragmented parent and daughter ions may be analyzed further for sequencing purposes. If, however, ion drift time overlap is observed in the first execution of step 412, process 400 continues from step 420 at step 422 where QMF 302 is configured to selectively filter out desired m/z values based on the observed overlapping drift times. Thereafter, the process counter A is incremented and steps 408–412 are repeated.

Referring now to FIGS. 15A–15D, step 422 and a second pass through steps 408, 410 and 412 are illustrated. The ion gate signal 450 and TOFMS signals 452 are identical to those shown in FIGS. 14A and 14B, but the QMF signal 458 includes an activation pulse $458_1$ during a time period encompassing the drift times of ions c and d, and an activation pulse $458_2$ encompassing the drift times of ions e and f. It is to be understood that activation pulses $458_1$ and $458_2$ are not meant to represent a single-signal activation of QMF 302 (i.e., "triggering"), but are instead meant to represent the activation times of QMS 302 relative to known ion drift times, wherein computer 302 is operable during each of these activation times to control the voltage sources $320_1$ and $320_2$ (FIG. 11), as described hereinabove, to thereby pass only ions having a desired m/z value and to filter out ions having any other m/z value. In the example spectrum illustrated in FIG. 15D, computer 310 is operable to control QMF 302 during activation time $458_1$ to pass only ions having m/z values equal to that of ion c so that ion d is effectively filtered out. Similarly, computer 310 is operable to control QMF 302 during activation time $458_2$ to pass only ions having m/z values equal to that of ion e so that ion f is effectively filtered out. In one preferred embodiment of process 400, computer 310 is operable at all other times in an all-pass mode to thereby pass therethrough ions having any m/z value. In an alternate embodiment, computer 310 may be operable to sequentially control QMF 302 during time periods corresponding to the drift times of each of the ions, wherein computer 310 is operable during such time periods to pass only ions having m/z values equal to those of interest. Thus, for the example spectrum 460 illustrated FIG. 15D, computer 310 may alternatively be operable to activate QMF 302 during the drift time of ion a to pass only ions having m/z values equal to that of ion a, to activate QMF 302 during the drift time of ion b to thereby pass only ions having m/z values equal to that of ion b, to activate QMF 302 during the drift time of ions c and d to pass only ions having m/z values equal to that of ion c, etc. In either case, the spectrum 460 of FIG. 15D results, wherein the flight times of each of the parent and daughter ions resulting from the fragmentation of ions a, b, c, e and g in collision cell 304 are clearly resolved. From these flight times, the m/z values of each of the fragmented ions may be determined in accordance with known techniques.

Referring again to FIG. 13, process 400 advances from a second execution of step 412 to step 414 where process 400 is directed to a process section flagged by the most recent value of the counting variable A. In this case, A=2 so process 400 is directed to step 426. Thereafter at step 428, a determination is made as to whether any ion packets exist that have not yet been accounted for in the spectrum 460 of FIG. 15D. In one preferred embodiment, step 428 is conducted manually via examination of spectra 456 and 460, although the present invention contemplates that step 428 may alternatively be automated in a known manner and accordingly be executed by computer 310. In any case, if it is determined at step 428 that no ion packets are unaccounted for, process 400 advances to step 432 where process 400 is terminated. If, on the other hand, it is determined at step 428 that there exists at least one ion packet that has not yet been accounted for in spectrum 460, process 400 advances to step 430 where QMF 302 is configured to selectively filter out desired m/z values based on the observed overlapping drift times. Thereafter, steps 408–412 are again repeated.

Referring now to FIGS. 16A–16D, step 430 and a third pass through steps 408, 410 and 412 are illustrated. The ion gate signal 450 and TOFMS signals 452 are identical to those shown in FIGS. 14A and 14B, but the QMF signal 462 includes an activation pulse $462_1$ during a time period encompassing the drift times of ions c and d, and an activation pulse $462_2$ encompassing the drift times of ions e and f. Again, it is to be understood that activation pulses $462_1$ and $462_2$ are not meant to represent a single-signal activation of QMF 302 (i.e., "triggering"), but are instead meant to represent the activation times of QMS 302 relative to known ion drift times, wherein computer 302 is operable during each of these activation times to control the voltage sources $320_1$ and $320_2$ (FIG. 11), as described hereinabove, to thereby pass only ions having a desired m/z value and to filter out ions having any other m/z value. In the example spectrum illustrated in FIG. 16D, computer 310 is operable to control QMF 302 during activation time $462_1$ to pass only ions having m/z values equal to that of ion d so that ion c is effectively filtered out. Similarly, computer 310 is operable to control QMF 302 during activation time $462_2$ to pass only ions having m/z values equal to that of ion f so that ion e is effectively filtered out. In one preferred embodiment of process 400, computer 310 is operable at all other times in a no-pass mode to thereby inhibit passage therethrough of ions having any m/z value. In an alternate embodiment, computer 310 may be operable to sequentially control QMF 302 during time periods corresponding to the drift times of each of the ions, wherein computer 310 is operable during such time periods to pass only ions having m/z values equal to those of interest. Thus, for the example spectrum 464 illustrated FIG. 16D, computer 310 may additionally be operable to activate QMF 302 during the drift times of ions a, b and g to pass only ions having m/z values equal to those of ions a, b and g respectively. This will result in redundant flight time information for parent/daughter ions of a, b and g, but such operation serves as an accuracy check on the data obtained from spectrum 464. In the first case, the spectrum 464 of FIG. 16D results, wherein the flight times of each of the parent and daughter ions resulting from the fragmentation of ions d and f in collision cell 304 are clearly resolved. In the latter case, a spectrum similar to spectrum 460 of FIG. 15D results, wherein the flight times of each of the parent and daughter ions resulting from the fragmentation of ions a, b, d, f and g in collision cell 304 are clearly resolved. In either case, the m/z values of each of the fragmented ions may be determined from their associated flight times in accordance with known techniques.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, referring to FIG. 17, alternative variations of the ion mobility and mass spectrometer instrument of FIG. 9 are illustrated, wherein ion trapping, ion mass filtering and ion fragmentation functions may, in accordance with the present invention, be positioned in various locations with respect to the ion source 32, ion mobility instrument 34 and time-of-flight mass spectrometer 36. In a first specific example, structure 500 represents a quadrupole mass filter, such as QMF 302 described hereinabove, structures 502 and 504 may be omitted, and structure 506 represents a collision cell such as collision cell 304. In this embodiment, ion mass selection is performed prior to injecting ions into IMS 34, and ion fragmentation is performed between IMS 34 and TOFMS 36. In a second specific example, structure 500 represents a quadrupole mass filter, such as QMF 302 described hereinabove, structure 502 represents an ion trap, such as ion trap 152 described hereinabove, structure 504 is omitted and structure 506 represents a collision cell such as collision cell 304 described hereinabove. In this embodiment, mass selection is performed upon ions generated by ion source 32 and the mass selected ions are collected in the ion trap 152 prior to injection into IMS 34. Fragmentation is performed in collision cell 304 as described hereinabove. Additionally, or alternatively, fragmentation may also be performed in ion trap 152, as-is known in the art, if ion trap 152 is supplied with a suitable buffer gas (not shown) and/or in IMS 34 as described hereinabove. In a third specific example, structure 500 represents a quadrupole mass filter, such as QMF 302 described hereinabove, structure 502 represents a collision cell such as collision cell 304 described hereinabove, and structures 504 and 506 are omitted. In this embodiment, mass selection is performed upon ions generated by ion source 32 and the mass selected ions are fragmented in collision cell 304 prior to injection into IMS 34. Fragmentation may additionally or alternatively be performed in IMS 34, and/or an additional collision cell 304 may be provided as structure 506 for further fragmenting the ions supplied by IMS 34. In a fourth specific example, structure 500 represents a quadrupole mass filter, such as QMF 302 described hereinabove, structure 502 represents an ion trap, such as ion trap 152 described hereinabove, structure 504 represents a collision cell, such as collision cell 304 described hereinabove, and structure 506 is omitted. In this embodiment, mass selection is performed upon ions generated by ion source 32, followed by collection of the mass filtered ions within ion trap 152, followed by fragmentation of the ions collected in trap 152 either within trap 152 and/or within collision cell 304 prior to injection of the ions into IMS 34. Further fragmentation may be performed within IMS 34 and/or structure 506 may define an additional collision cell for further ion fragmentation prior to injection of the ions into TOFMS 36. Generally, it is to be understood that ion mass selection and ion fragmentation may occur at various and multiple locations relative to ion source 32, IMS 34 and TOFMS 36. Moreover, it is to be understood that IMS 34 may be generally configured as a known gas chromatograph, as illustrated hereinabove, or alternatively as a known liquid chromatograph, without detracting from the scope of the present invention.

Figure 17:
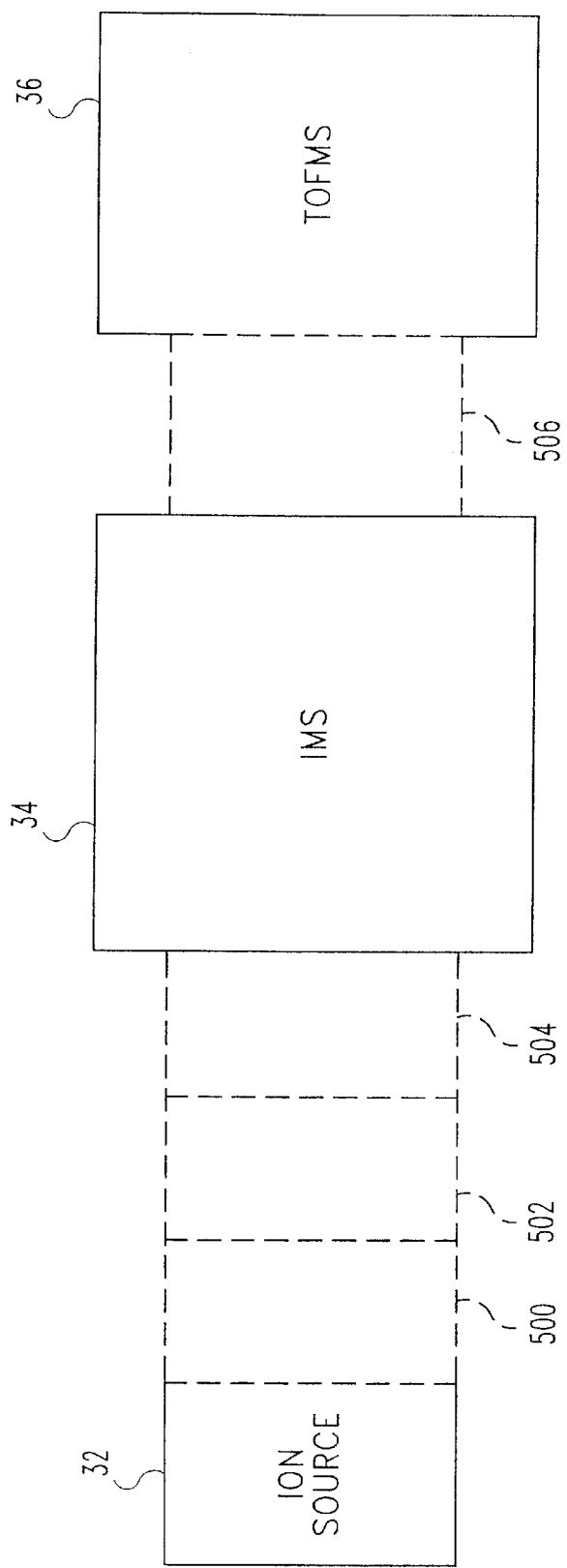
FIG. 17 is a block diagram illustrating alternative structural variations of the ion mobility and time-of-flight mass spectrometer of the present invention.
Figure 18:
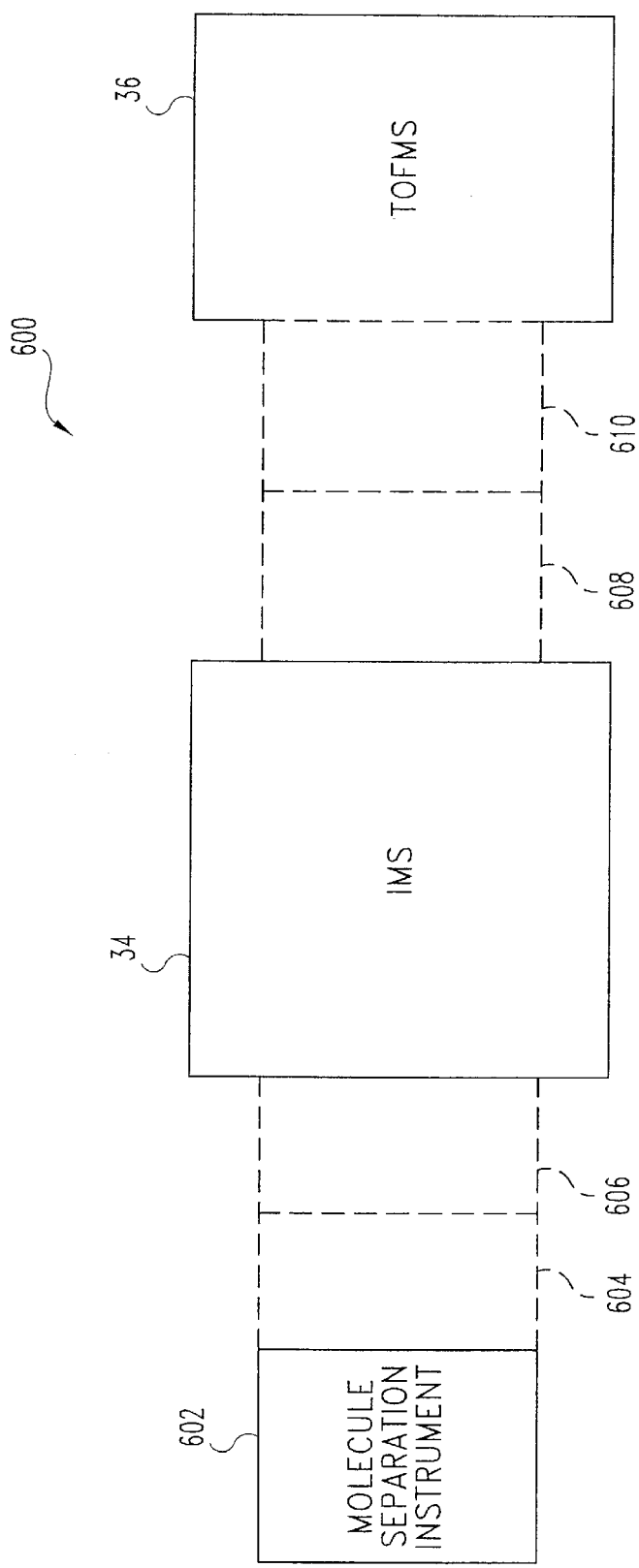
FIG. 18 is a block diagram illustrating further alternative structural variations of the ion mobility and time-of-flight mass spectrometer of the present invention.

Referring now to FIG. 18, another alternative embodiment 600 of the ion mobility and mass spectrometer instrument 600 of the present invention is shown. In accordance with this aspect of the invention, a molecule separation instrument 602 serves as an ion source coupled to the ion mobility spectrometer (IMS) instrument 34 that is, in turn, coupled to the time-of-flight mass spectrometer (TOFMS) instrument 34. Any one or more of the ion mass filtering, ion trapping and ion fragmentation functions may be interposed between the molecule separation unit 602 and the IMS 34 and/or between the TOFMS 36, and some specific examples of such combinations will be described in greater detail hereinafter. It should be understood, however, that specific descriptions of such combinations (as with the instrumentation shown and described with respect to FIG. 17) will be described by way of example only, and that other combinations of instrumentation described herein are intended to fall within the scope of the present invention. It should also be understood that while FIGS. 17 and 18 are illustrated simply as various combinations of functional blocks, actual implementations of such combinations will typically require computer control of one or more of the individual components included therein via voltage sources, one or more buffer gases, one or more vacuum pumps, and the like as shown and described with respect to one or more of the various embodiments of the present invention. Such control hardware has been described in detail hereinabove and has therefore been omitted from FIGS. 17 and 18 for brevity; it being further understood that the various components of the instruments shown in FIGS. 17 and 18 may be operable as described hereinabove and in any one or more of the operational modes described therefore.

In any case, in a first specific embodiment of the instrument 600 shown in FIG. 18, components 604–610 are omitted and the molecule separation instrument 602 may be any known instrument operable to separate molecules over time as a function of a predefined molecular characteristic. With these combined instrument components, the resulting instrument 600 is thus operable to provide additional, or at least different, molecular information in a time sequence over any of the instruments previously described hereinabove. In this embodiment, the molecule separation instrument 602 may use any one or more of the ion sources (74, 74', 74'', 74''') or ion source regions (32, and including the gated collection chamber arrangement 354 shown in FIG. 10) for generating ions for separation according to the predefined molecular characteristic. Alternatively, instrument 602 may use any known molecule or ion generating technique specific thereto, or may alternatively still use any other known molecule or ion generating technique for generating ions for separation according to the predefined molecular characteristic.

In one embodiment, molecule separation instrument 602 is a mass spectrometer of known construction such as, for example, TOFMS 36. In this embodiment, ions from a suitable source are first separated in time by instrument 602 according to ion mass/charge, then in time by IMS 34 as a function of ion mobility, and then again in time by TOFMS 36 as a function of ion mass/charge. In an alternate embodiment, molecule separation instrument 602 is an ion mobility instrument of known construction such as, for example, IMS 34. In this embodiment, ions from a suitable source are first separated in time by IMS 34 as a function of ion mobility, and then again in time as a function of ion mobility, and then in time as a function of ion mass/charge. In this embodiment, the two cascaded ion mobility instruments 602 and 34 are preferably configured at least slightly differently to thereby each provide correspondingly different ion mobility vs. time information, and examples of a number of such different configurations will be described in greater detail hereinafter with respect to FIG. 19.

In still another embodiment, the molecule separation instrument 602 may be any known instrument or process that is operable to separate molecules in time as a function of some dimension that is neither ion mobility nor ion mass/charge to thereby provide for additional molecular information over that available using any combination of the techniques described hereinabove. In other words, with the combined instrumentation just described, molecular information may be obtained in a time sequence that includes ion mass/charge information, ion mobility information and ion information separated in time as a function of some other molecular property or characteristic. As one specific example, the molecule separation instrument 602 may be a known liquid chromatography instrument operable to separate ions from a suitable source over time as a function of molecule retention time (or inversely, molecule migration rate), as is known in the art. As another example, the molecule separation instrument 602 may be a known gas chromatography instrument, also operable to separate ions from a suitable source over time as a function of retention time or migration rate. Generally, the present invention contemplates that the molecule separation instrument 602 may be any molecule separation instrument, including any known chromatography instrument, operable to separate molecules (ions, specifically) over time in a dimension that is neither ion mobility nor ion mass/charge, and any such instrumentation is intended to fall within the scope of the present invention.

In another specific embodiment of the instrument 600 illustrated in FIG. 18, components 606–610 are omitted, the molecule separation instrument 602 may be any one or combination of molecule instruments described hereinabove, and component 604 is an ion fragmentation unit such as a collision cell. Component 604 may accordingly include, for example, a collision cell such as collision cell 304 and a source of buffer or other ion collision promoting gas such as gas source 46 or 306, all as illustrated in FIG. 9. In this embodiment, at least some of the ions separated in time by molecule separation instrument 602 are directed into ion fragmentation unit 604 where they undergo collisions with an appropriate buffer gas and fragment into daughter ions as described hereinabove with respect to the description of collision cell 304. At least some of the daughter ions are then directed into IMS 34 for separation in time according to ion mobility, and at least some of the ions separated in time according to ion mobility are then directed into TOFMS 36 for separation in time according to ion mass/charge. With most source samples, the inclusion of fragmentation unit 604 thus provides for even more molecular information than that available with only instruments 602, 34 and 36.

In yet another specific embodiment of the instrument 600 illustrated in FIG. 18, components 604, 608 and 610 are omitted, the molecule separation instrument 602 may be any one or combination of molecule instruments described hereinabove, and component 606 is an ion mass filtering unit such as a quadrupole mass filter 302 as illustrated in FIGS. 9 and 11–12. In this embodiment, at least some of the ions separated in time by molecule separation instrument 602 are directed into ion mass filter 606, wherein mass filter 606 is controlled as described hereinabove with respect to the description of quadrupole mass filter 302, to allow passage therethrough only of ions having desired mass-to-charge ratios. At least some of the ions passing through the ion mass filter 606 are then directed into IMS 34 for separation in time according to ion mobility, and at least some of the ions separated in time according to ion mobility are then directed into TOFMS 36 for separation in time according to ion mass/charge. The inclusion of ion mass filter 606 thus allows for selective analysis only of ions of interest; i.e., only of ions having desired mass-to-charge ratios.

In still another specific embodiment of the instrument 600 illustrated in FIG. 18, components 608 and 610 are omitted, the molecule separation instrument 602 may be any one or combination of molecule instruments described hereinabove. Component 604 may be either an ion fragmentation unit, such as a collision cell arrangement as shown in FIG. 9 including collision cell 304 and buffer gas source 46 or 306, or an ion mass filtering unit such as quadrupole mass filter 302. If component 604 is an ion fragmentation unit, then component 606 is preferably an ion mass filtering unit such as quadrupole mass filter 302. In this embodiment, at least some of the ions separated in time by molecule separation instrument 602 are directed into ion fragmentation unit 604 where they undergo collisions with an appropriate buffer gas and fragment into daughter ions as described hereinabove with respect to the description of collision cell 304. At least some of the daughter ions are then directed into ion mass filter 606, wherein mass filter 606 is controlled as described hereinabove with respect to the description of quadrupole mass filter 302, to allow passage therethrough only of daughter ions having desired mass-to-charge ratios. At least some of the ions passing through the ion mass filter 606 are then directed into IMS 34 for separation in time according to ion mobility, and at least some of the ions separated in time according to ion mobility are then directed into TOFMS 36 for separation in time according to ion mass/charge. The foregoing arrangement inclusion thus allows for selective analysis only of fragmented ions of interest; i.e., only of ions having desired mass-to-charge ratios. If, on the other hand, component 604 is an ion mass filtering unit, then component 606 is preferably an ion fragmentation unit such as the collision cell arrangement shown in FIG. 9 including collision cell 304 and buffer gas source 46 or 306. In this embodiment, at least some of the ions separated in time by molecule separation instrument 602 are directed into ion mass filtering unit 604, wherein mass filter 604 is controlled as described hereinabove with respect to the description of quadrupole mass filter 302, to allow passage therethrough only of ions having desired mass-to-charge ratios. At least some of the ions passing through ion mass filtering unit 604 are then directed into fragmentation unit 606 where they undergo collisions with an appropriate buffer gas and fragment into daughter ions as described hereinabove with respect to the description of collision cell 304. At least some of these fragmented ions are then directed into IMS 34 for separation in time according to ion mobility, and at least some of the ions separated in time according to ion mobility are then directed into TOFMS 36 for separation in time according to ion mass/charge. The foregoing arrangement thus allows for fragmentation and subsequent spectral analysis only of ions of interest; i.e., only of ions having desired mass-to-charge ratios.

In a further embodiment of the instrument 600 illustrated in FIG. 18, components 604–608 are omitted, the molecule separation instrument 602 may be any one or combination of molecule instruments described hereinabove, and component 610 is an ion fragmentation unit such as a collision cell. Component 610 may accordingly include, for example, a collision cell such as collision cell 304 and a source of buffer or other ion collision promoting gas such as gas source 46 or 306, all as illustrated in FIG. 9. In this embodiment, at least some of the ions separated in time by molecule separation instrument 602 are directed into IMS 34 for separation in time according to ion mobility, and at least some of the ions separated in time according to ion mobility are then directed into ion fragmentation unit 604 where they undergo collisions with an appropriate buffer gas and fragment into daughter ions as described hereinabove with respect to the description of collision cell 304. At least some of the daughter ions are then directed into TOFMS 36 for separation in time according to ion mass/charge. This arrangement provides the ability to further fragment ions that have been sequentially separated in time according to the predefined molecular characteristic and then according to ion mobility, prior to separation in time according to ion mass-to-charge ratio. With most source samples, the inclusion of fragmentation unit 610 thus provides for even more molecular information than that available with only instruments 602, 34 and 36.

In yet a further specific embodiment of the instrument 600 illustrated in FIG. 18, components 604, 606 and 610 are omitted, the molecule separation instrument 602 may be any one or combination of molecule instruments described hereinabove, and component 608 is an ion mass filtering unit such as a quadrupole mass filter 302 as illustrated in FIGS. 9 and 11–12. In this embodiment, at least some of the ions separated in time by molecule separation instrument 602 are directed into IMS 34 for separation in time according to ion mobility, and at least some of the ions separated in time according to ion mobility are then directed into ion mass filter 606, wherein mass filter 606 is controlled as described hereinabove with respect to the description of quadrupole mass filter 302, to allow passage therethrough only of ions having desired mass-to-charge ratios. At least some of the ions passing through the ion mass filter 606 are then directed into TOFMS 36 for separation in time according to ion mass/charge. The inclusion of ion mass filter 608 thus allows for selective analysis only of ions of interest; i.e., only of ions having desired mass-to-charge ratios.

In still a further specific embodiment of the instrument 600 illustrated in FIG. 18, components 604 and 606 are omitted, the molecule separation instrument 602 may be any one or combination of molecule instruments described hereinabove. Component 608 may be either an ion fragmentation unit, such as a collision cell arrangement as shown in FIG. 9 including collision cell 304 and buffer gas source 46 or 306, or an ion mass filtering unit such as quadrupole mass filter 302. If component 608 is an ion fragmentation unit, then component 610 is preferably an ion mass filtering unit such as quadrupole mass filter 302. In this embodiment, at least some of the ions separated in time by molecule separation instrument 602 are directed into IMS 34 for separation in time according to ion mobility. At least some of the ions separated in time according to ion mobility are then directed into ion fragmentation unit 608 where they undergo collisions with an appropriate buffer gas and fragment into daughter ions as described hereinabove with respect to the description of collision cell 304. At least some of the daughter ions are then directed into ion mass filter 610, wherein mass filter 610 is controlled as described hereinabove with respect to the description of quadrupole mass filter 302, to allow passage therethrough only of daughter ions having desired mass-to-charge ratios. At least some of the ions passing through the ion mass filter 606 are then directed into TOFMS 36 for separation in time according to ion mass/charge. The foregoing arrangement inclusion thus allows for selective analysis only of fragmented ions of interest; i.e., only of ions having desired mass-to-charge ratios. If, on the other hand, component 608 is an ion mass filtering unit, then component 610 is preferably an ion fragmentation unit such as the collision cell arrangement shown in FIG. 9 including collision cell 304 and buffer gas source 46 or 306. In this embodiment, at least some of the ions separated in time by molecule separation instrument 602 are directed into IMS 34 for separation in time according to ion mobility. At least some of the ions separated in time according to ion mobility are then directed into ion mass filtering unit 608, wherein mass filter 608 is controlled as described hereinabove with respect to the description of quadrupole mass filter 302, to allow passage therethrough only of ions having desired mass-to-charge ratios. At least some of ions passing through ion mass filtering unit 608 are then directed into fragmentation unit 610 where they undergo collisions with an appropriate buffer gas and fragment into daughter ions as described hereinabove with respect to the description of collision cell 304. At least some of ions passing through ion mass filtering unit 610 are then directed into TOFMS 36 for separation in time according to ion mass/charge. The foregoing arrangement thus allows for fragmentation and subsequent spectral analysis only of ions of interest; i.e., only of ions having desired mass-to-charge ratios.

In still another embodiment of the instrument 600 illustrated in FIG. 18, molecule separation unit 602, as described hereinabove, IMS 34 and TOFMS 36 are included, and any combination of components 604–610, as each are described hereinabove, may also be included. Those skilled in the art will recognize specific combinations of components 604–610 that may be of interest, and any such combinations are intended to fall within the scope of the present invention.

Figure 19:
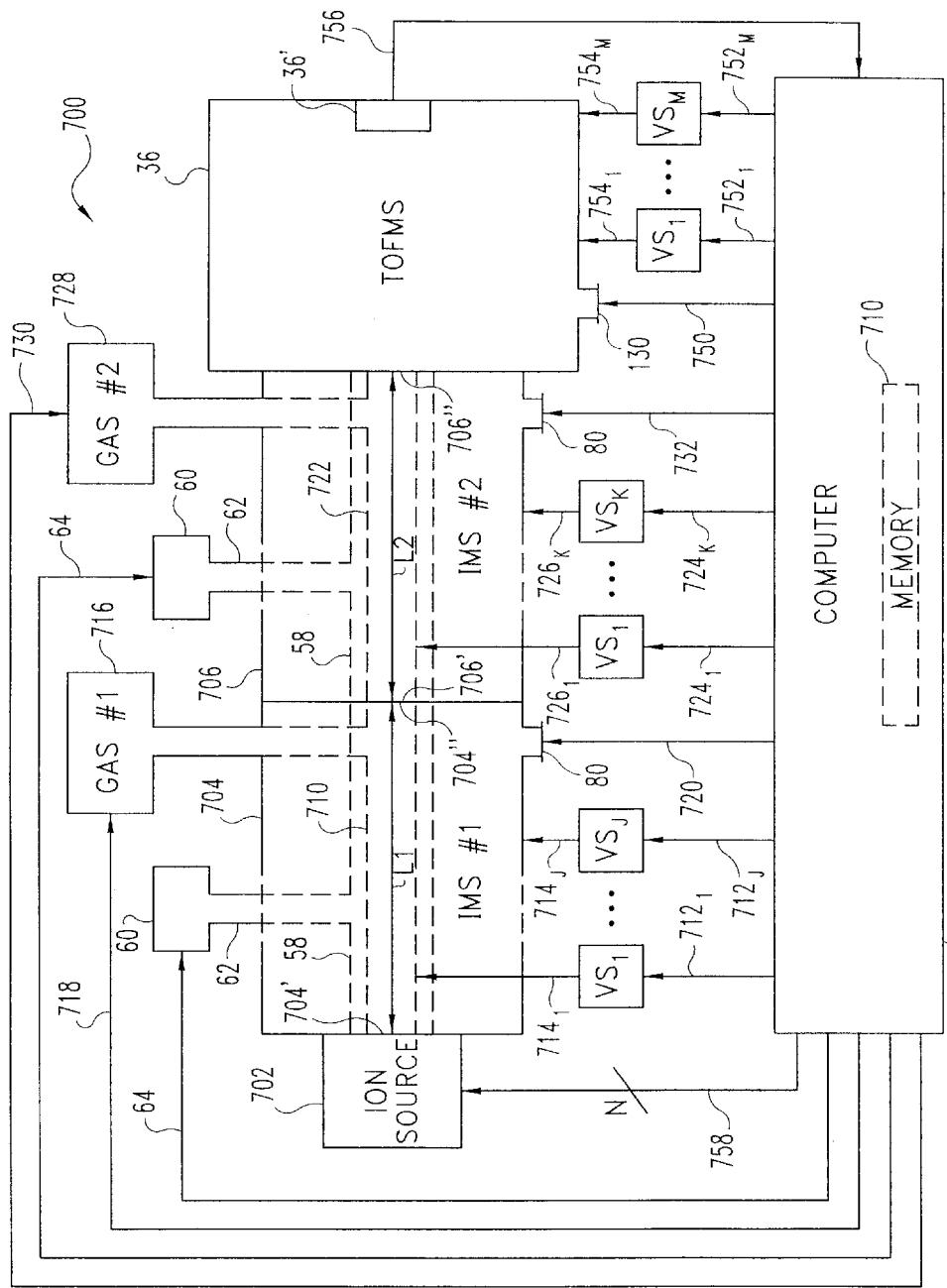
FIG. 19 is a block diagram illustration of yet another alternate embodiment of an ion mobility and time-of-flight mass spectrometer, in accordance with the present invention.

Referring now to FIG. 19, another preferred embodiment 700 of the ion mobility and mass spectrometer instrument of the present invention is shown. In accordance with this aspect of the present invention, two cascaded ion mobility instruments 704 (IMS #1) and 706 (IMS #2) are disposed between an ion source 702 and a mass spectrometer 36, wherein mass spectrometer 36 may be any known mass spectrometer instrument as described hereinabove. Ion source 702 may be any one, or combination of, the various ion sources 74, 74', 74" and 74'" or ions source regions 32 (including the ion source arrangement illustrated in FIG. 10 including ion collection chamber 354) described hereinabove. Alternatively or additionally, ion source 702 may include a molecule separation instrument, such as instrument 602 shown and described with respect to FIG. 18, whereby ions previously separated in time according to a predefined molecular characteristic such as ion retention time, for example, are sequentially introduced into IMS 704. A computer 708 is included for controlling instrument 700, which is preferably at least structurally equivalent to computer 38 (FIGS. 4 and 5) or computer 310 (FIG. 9), and includes a memory 710 preferably having stored therein information relating to the operation of instrument 700 and including sufficient storage capacity for storing information generated by instrument 700. Computer 708 includes an output electrically connected to ion source 702 via a number, N, of signal paths 758, wherein N may be any positive integer, and whereby computer 708 is operable to control ion source 702 as described hereinabove with respect to any of the various embodiments thereof. Computer 708 further includes an input electrically connected to an output of an ion detector 36' of mass spectrometer 36 via signal path 756, whereby computer 708 is responsive to an ion detection signal provided on signal path 756 by detector 36' to determine information relating to ion travel through instrument 700.

The first ion mobility instrument 704 has an ion inlet 704' coupled to an ion outlet of ion source 702, an ion outlet 704" and an ion drift tube 710 (shown in phantom) of length L1 defined therebetween, wherein drift tube 710 may be structurally equivalent to drift tube 40 described with respect to IMS 34 of FIG. 4. A number, J, of outputs of computer 708 are electrically connected to a corresponding number of voltage sources $VS_1$–$VS_J$ via respective signal paths $712_1$–$712_J$, wherein J may be any positive integer. Voltage sources $VS_1$–$VS_J$ are, in turn, electrically connected to instrument 704 via respective signal paths $714_1$–$714_J$, whereby computer 708 is operable to control the operation of instrument 704 via appropriate control of voltage sources $VS_1$–$VS_J$ as described hereinabove. At least one such voltage source (e.g., $VS_1$) is electrically connected to the drift tube 710 as described with respect to FIG. 4, wherein computer 708 is operable to control the voltage thereof to thereby establish and control a resultant electric field within drift tube 710.

Drift tube 710 is also fluidly coupled to a source 716 of gas (gas #1), wherein gas #1 is preferably a known buffer gas, but may alternatively be another gas including ambient air, and is further fluidly coupled to a vacuum pump 80. Gas source 716 is electrically connected to an output of computer 708 via signal path 718, and vacuum pump 80 is electrically connected to an output of computer 708 via signal path 720, whereby computer 708 is operable to control the flow of gas #1 into and out of instrument 704 as described hereinabove.

Drift tube 710 is further surrounded by a variable temperature housing 58 connected to a variable temperature source 60 via path 62. An output of computer 708 is electrically connected to variable temperature source 60 via signal path 64 and is operable to control temperature source 60 to thereby control the temperature of the interior of drift tube 710 as described hereinabove with respect to FIG. 4.

The second ion mobility instrument 706 has an ion inlet 706' coupled to ion outlet 704" of instrument 704, an ion outlet 706" and an ion drift tube 722 (shown in phantom) of length L2 defined therebetween, wherein drift tube 722 may be structurally equivalent to drift tube 40 described with respect to IMS 34 of FIG. 4. A number, K, of outputs of computer 708 are electrically connected to a corresponding number of voltage sources $VS_1$–$VS_K$ via respective signal paths $724_1$–$724_K$, wherein K may be any positive integer. Voltage sources $VS_1$–$VS_K$ are, in turn, electrically connected to instrument 706 via respective signal paths $726_1$–$726_K$, whereby computer 708 is operable to control the operation of instrument 706 via appropriate control of voltage sources $VS_1$–$VS_K$ as described hereinabove. At least one such voltage source (e.g., $VS_1$) is electrically connected to the drift tube 722 as described with respect to FIG. 4, wherein computer 708 is operable to control the voltage thereof to thereby establish and control a resultant electric field within drift tube 722.

Drift tube 722 is also fluidly coupled to a source 728 of gas (gas #2), wherein gas #2 is preferably a known buffer gas, but may alternatively be another gas including ambient air, and is further fluidly coupled to a vacuum pump 80. Gas source 728 is electrically connected to an output of computer 708 via signal path 730, and vacuum pump 80 is electrically connected to an output of computer 708 via signal path 732, whereby computer 708 is operable to control the flow of gas #2 into and out of instrument 706 as described hereinabove.

Drift tube 722 is further surrounded by a variable temperature housing 58 connected to a variable temperature source 60 via path 62. An output of computer 708 is electrically connected to variable temperature source 60 via signal path 64 and is operable to control temperature source 60 to thereby control the temperature of the interior of drift tube 722 as described hereinabove with respect to FIG. 4.

TOFMS 36 includes a vacuum pump 130 electrically connected to an output of computer 708 via signal path 750, whereby computer 708 is operable to control pump 130 to thereby establish and control a vacuum level within TOFMS 36. A number, M, of outputs of computer 708 are electrically connected to a corresponding number of voltage sources $VS_1$–$VS_M$ via respective signal paths $752_1$–$752_M$, wherein M may be any positive integer. Voltage sources $VS_1$–$VS_M$ are, in turn, electrically connected to instrument 36 via respective signal paths $754_1$–$754_M$, whereby computer 708 is operable to control the operation of instrument 36 via appropriate control of voltage sources $VS_1$–$VS_M$ as described hereinabove. It is to be understood that while the control of gases, temperatures, voltage sources, vacuum pumps and the like have been shown and described with respect to FIG. 19 as being computer controlled, any one or more such parameters and structures may alternatively be controlled manually.

In accordance with the present invention, ion mobility spectrometers 704 and 706 may be configured differently from each other to thereby provide additional or expanded molecular information over that available with a single IMS system such as those shown in FIGS. 4, 5 and 9. In one embodiment, for example, instruments 704 and 706 are configured such that the length L1 of instrument 704 is different from the length L2 of instrument 706. As a specific example of this embodiment, L1 is preferably greater than L2 so that instruments 704, 706 and 36 may be operated with a sequence of increasing sampling rates to thereby produce three-dimensional molecular information. In this embodiment, for example, L1 may be sized such that ion drift time therethrough is on the order of seconds, L2 may be sized such that ion drift time therethrough is on the order of milli-seconds, and TOFMS 36 may be configured such that ion flight time therethrough is on the order of micro-seconds. Ion packets traveling through instrument 700 are thus subjected to increased sampling rates, which results in multi-dimensional molecular information.

In an alternate embodiment of instrument 700, the variable temperature sources 60 of the ion mobility spectrometers 704 and 706 are controlled such that the temperature, T1, of drift tube 710 is different than the temperature, T2, of drift tube 722. Generally, the collision cross-section (collision integral), and hence ion mobility, changes at elevated temperatures more so than at lower temperatures. Thus, by operating instruments 704 and 706 at different drift tube temperatures, ion packets traveling through instrument 700 are thus subjected to three different separation criteria, which results in multi-dimensional molecular information. In a further embodiment, either one or both of the variable temperature sources 60 of ion mobility spectrometers 704 and 706 may be controlled to establish a temperature gradient through a corresponding one or both of the spectrometers 704 and 706. This feature allows for an additional degree of ion separation and may also be used with a single ion mobility spectrometer instrument of the type described hereinabove.

In another alternate embodiment of instrument 700, the electric fields established within drift tubes 710 and 722 are controlled, as described hereinabove, such that the electric field, E1, within drift tube 710 is different from the electric field, E2, within drift tube 722. At low electric fields, the ratio of electric field and buffer gas concentration is also low, and molecular collisions with the buffer gas does not result in any significant temperature change. At high electric fields, however, the ratio of electric field and buffer gas concentration is high, and molecular collisions with the buffer gas result in the generation of heat which, as just described, changes the collision integral. By operating instruments 704 and 706 with different drift tube electric fields, wherein the electric field in one of the drift tubes is at least high enough to result in the generation of heat due to collisions of ions with the corresponding buffer gas, ion packets traveling through instrument 700 are thus subjected to three different separation criteria, which results in multi-dimensional molecular information. In accordance with the present invention, one of the electric fields E1 and E2 may be a zero electric field while the other is nonzero, or alternatively, both electric fields E1 and E2 may be non-zero fields. In a further embodiment, either one or both of the electric fields E1 and E2 may be configured as an electric field gradient to thereby establish an electric field gradient through a corresponding one or both of the spectrometers 704 and 706. This feature allows for an additional degree of ion separation and may also be used with a single ion mobility spectrometer instrument of the type described hereinabove.

In still another alternate embodiment of instrument 700, the gases established within drift tubes 710 and 722 are chosen such that gas #1 within drift tube 710 is different from gas #2 within drift tube 722. Generally, the collision integral is different for different buffer gases, and by operating instruments 704 and 706 with different gases within the respective drift tubes 710 and 722, ion packets traveling through instrument 700 are thus subjected to three different separation criteria, which results in multi-dimensional molecular information. In accordance with the present invention, either gas #1 or gas #2 may be ambient air while the other gas is a known buffer gas, or alternatively, gas #1 may be a first known buffer gas and gas #2 may be a second known buffer gas different from gas #1.

It is to be understood that instrument 700 may be configured with any combination of the foregoing configurations of instruments 704 and 706, and all such combinations are intended to fall within the scope of the present invention.

What is claimed is:

1. A method of separating ions in time, comprising the steps of:
   separating a bulk of ions in time according to a first function of ion mobility;
   sequentially separating in time according to a second function of ion mobility at least some of said ions separated in time according to said first function of ion mobility, said second function of ion mobility different from said first function of mobility;
   sequentially separating in time as a function of ion mass at least some of said ions separated in time according to said second function of ion mobility; and
   processing the ions separated in time as a function of ion mass to produce three-dimensional mass spectrum information for at least some of said bulk of ions separated in time as a function of said first function of ion mobility, said second function of ion mobility and ion mass.

2. The method of claim 1 further including the step of generating said bulk of ions for subsequent separation thereof according to said first function of ion mobility.

3. The method of claim 2 wherein the step of generating said bulk of ions includes generating said bulk of ions via electrospray ionization.

4. The method of claim 2 wherein the step of generating said bulk of ions includes desorbing said bulk of ions from a surface of a sample.

5. The method of claim 2 wherein the step of generating said bulk of ions includes the steps of:
   generating ions from a sample source;
   collecting at least some of said generated ions; and
   repeating the generating and collecting steps a number of times to form said bulk of ions.

6. The method of claim 2 wherein the step of generating said bulk of ions includes the steps of:
   continually generating ions from a sample source; and
   collecting a number of said continually generated ions to form said bulk of ions.

7. The method of claim 1 wherein the step of generating said bulk of ions includes separating a number of ions in time according to a predefined molecular characteristic.

8. The method of claim 1 wherein said predefined molecular characteristic is ion retention time.

9. The method of claim 1 wherein said first ion mobility function corresponds to a first length of ion drift and said second mobility function corresponds to a second length of ion drift different from said first length of ion drift.

10. The method of claim 1 wherein said first ion mobility function corresponds to separating said bulk of ions at a first temperature; and wherein said second ion mobility function corresponds to separating at least some of said ions previously separated in time according to said first function of ion mobility at a second temperature different from said first temperature.

11. The method of claim 1 wherein said first ion mobility function corresponds to separating said bulk of ions under the influence of a first electric field; and wherein said second ion mobility function corresponds to separating at least some of said ions previously separated in time according to said first function of ion mobility under the influence of a second electric field different from said first electric field.

12. The method of claim 11 wherein one of said first and second electric fields is a non-zero electric field and the other of said first and second electric fields is a zero electric field.

13. The method of claim 11 wherein said first and second electric fields are both non-zero electric fields.

14. The method of claim 11 wherein said first ion mobility function corresponds to separating said bulk of ions in the presence of a first gas;
   and wherein said second ion mobility function corresponds to separating at least some of said ions previously separated in time according to said first function of ion mobility in the presence of a second gas different from said first gas.

15. The method of claim 14 wherein one of said first and second gases is a buffer gas and the other of said first and second gases is ambient air.

16. The method of claim 14 wherein said first gas is a first buffer gas and said second gas is a second buffer gas.

17. Apparatus for separating ions in time, comprising:
   a first ion mobility spectrometer (IMS1) having an ion inlet and an ion outlet, said IMS1 operable to separate ions in time according to a first function of ion mobility;
   a second ion mobility spectrometer (IMS2) having an ion inlet coupled to said ion outlet of said IMS1 and an ion outlet, said IMS2 operable to separate ions in time according to a second function of ion mobility different from said first function of ion mobility;
   a mass spectrometer having an ion acceleration region coupled to said ion outlet of said IMS2 and an ion detector producing an ion signal as a function of ions detected thereat, said mass spectrometer operable to separate ions in time as a function of ion mass; and
   a computer having an input connected to said ion detector of said mass spectrometer, said computer processing said ion signal to produce three-dimensional mass spectrum information for at least some of said bulk of ions separated in time a function of said first function of ion mobility, said second function of ion mobility and ion mass.

18. The apparatus of claim 17 wherein said IMS1 includes a first ion drift tube defining a first length;
and wherein said IMS2 includes a second ion drift tube defining a second length different from said first length;
and wherein said first function of ion mobility corresponds to said first length of said first ion drift tube and said second function of ion mobility corresponds to said second length of said second ion drift tube.

19. The apparatus of claim 17 wherein said IMS1 includes a first temperature source operable to force an ion drift path of said IMS1 to a first temperature;
and wherein said IMS2 includes a second temperature source operable to force an ion drift path of said IMS2 to a second temperature different from said first temperature;
and wherein said first function of ion mobility corresponds to said first temperature and said second function of ion mobility corresponds to said second temperature.

20. The apparatus of claim 17 wherein said IMS1 includes means for establishing a first electric field within an ion drift path of said IMS1;
and wherein said IMS2 includes means for establishing a second electric field within an ion drift path of said IMS2, said first electric field different from said second electric field;
and wherein said first function of ion mobility corresponds to said first electric field and said second function of ion mobility corresponds to said second electric field.

21. The apparatus of claim 20 wherein one of said first and second electric fields is a zero electric field and the other one of said first and second electric fields is a non-zero electric field.

22. The apparatus of claim 20 wherein said first and second electric fields are both non-zero electric fields.

23. The apparatus of claim 17 wherein said IMS1 includes means for establishing a first gas within an ion drift path of said IMS1;
and wherein said IMS2 includes means for establishing a second gas within an ion drift path of said IMS2, said first gas different from said second gas;
and wherein said first function of ion mobility corresponds to said first gas and said second function of ion mobility corresponds to said second gas.

24. The apparatus of claim 23 wherein one of said first and second gases is a buffer gas and the other of said first and second gases is ambient air.

25. The apparatus of claim 23 wherein said first and second gases are both buffer gases.

26. The apparatus of claim 17 further including means for generating a bulk of ions;
wherein said IMS1 is operable to separate at least some of said bulk of ions in time according to said first function of ion mobility, said second IMS is operable to separate in time according to said second function of ion mobility at least some of said ions separated in time according to said first function of ion mobility, and said mass spectrometer is operable to separate in time according to ion mass at least some of said ions previously separated in time according to said second function of ion mobility.

27. The apparatus of claim 26 wherein said means for generating a bulk of ions includes means for separating ions in time as a function of a first molecular characteristic prior to separation of said ions in time by said IMS1.

28. The apparatus of claim 27 wherein said means for separating ions in time as a function of a first molecular characteristic includes means for separating said ions in time as a function of ion retention time.

29. A method of separating ions in time, comprising the steps of:
separating a bulk of ions in time as a function of ion mobility in the presence of a first electric field;
sequentially separating in time as a function of ion mobility in the presence of a second electric field different from said first electric at least some of said ions separated in time as a function of ion mobility in the presence of said first electric field; and
sequentially separating in time as a function of ion mass at least some of said ions separated in time as a function of ion mobility in the presence of said second electric field.

30. The method of claim 29 further including the step of processing the ions separated in time as a function of ion mass to produce three-dimensional mass spectrum information for at least some of said bulk of ions separated in time as a function of ion mobility in the presence of said first electric field, ion mobility in the presence of said second electric field and ion mass.

31. The method of claim 29 further including the step of generating said bulk of ions for subsequent separation thereof according to ion mobility in the presence of said first electric field.

32. The method of claim 31 wherein the step of generating said bulk of ions includes generating said bulk of ions via electrospray ionization.

33. The method of claim 31 wherein the step of generating said bulk of ions includes desorbing said bulk of ions from a surface of a sample.

34. The method of claim 31 wherein the step of generating said bulk of ions includes the steps of:
generating ions from a sample source;
collecting at least some of said generated ions; and
repeating the generating and collecting steps a number of times to form said bulk of ions.

35. The method of claim 31 wherein the step of generating said bulk of ions includes the steps of:
continually generating ions from a sample source; and
collecting a number of said continually generated ions to form said bulk of ions.

36. The method of claim 31 wherein the step of generating said bulk of ions includes separating a number of ions in time according to a predefined molecular characteristic.

37. The method of claim 36 wherein said predefined molecular characteristic is ion retention time.

38. Apparatus for separating ions in time, comprising:
a first ion mobility spectrometer (IMS1) having an ion inlet and an ion outlet, said IMS1 operable to separate ions in time in the presence of a first electric field;
a second ion mobility spectrometer (IMS2) having an ion inlet coupled to said ion outlet of said IMS1 and an ion outlet, said IMS2 operable to separate ions in time in the presence of a second electric field different from said first electric field; and a mass spectrometer having an ion acceleration region coupled to said ion outlet of said IMS2 and an ion detector producing an ion signal as a function of ions detected thereat, said mass spectrometer operable to separate ions in time as a function of ion mass.

39. The apparatus of claim 38 wherein one of said first and second electric fields is a zero electric field and the other one of said first and second electric fields is a non-zero electric field.

40. The apparatus of claim 38 wherein said first and second electric fields are both non-zero electric fields.

41. The apparatus of claim 38 further including a computer having an input connected to said ion detector of said mass spectrometer, said computer processing said ion signal to produce a three-dimensional representation of at least some of said bulk of ions separated in time as a function of ion mobility in the presence of said first electric field, ion mobility in the presence of said second electric field and ion mass.

42. The apparatus of claim 38 further including means for generating a bulk of ions; wherein said IMS1 is operable to separate said bulk of ions in time as a function of ion mobility in the presence of said first electric field, said second IMS is operable to separate in time as a function of ion mobility in the presence of said second electric field at least some of said ions separated in time as a function of ion mobility in the presence of said first electric field, and said mass spectrometer is operable to separate in time as a function of ion mass at least some of said ions previously separated in time as a function of ion mobility in the presence of said second electric field.

43. The apparatus of claim 42 wherein said means for generating a bulk of ions includes means for separating ions in time as a function of a first molecular characteristic prior to separation of said ions in time by said IMS1.

44. The apparatus of claim 43 wherein said means for separating ions in time as a function of a first molecular characteristic includes means for separating said ions in time as a function of ion retention time.

* * * * *